(12) United States Patent
Swenson

(10) Patent No.: US 6,855,128 B2
(45) Date of Patent: Feb. 15, 2005

(54) DUAL BLUNTING NEEDLE ASSEMBLY

(75) Inventor: Kirk D. Swenson, North Caldwell, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 140 days.

(21) Appl. No.: 10/236,222

(22) Filed: Sep. 6, 2002

(65) Prior Publication Data

US 2003/0060772 A1 Mar. 27, 2003

Related U.S. Application Data

(60) Provisional application No. 60/324,814, filed on Sep. 25, 2001.

(51) Int. Cl.⁷ .................................................. A61M 5/00
(52) U.S. Cl. ............. 604/110; 604/164.01; 604/164.08; 604/170.02; 604/413; 600/573; 600/576; 600/577
(58) Field of Search .................. 604/19, 73.01, 604/110, 131, 140, 148, 149, 164.01, 164.12, 165.01, 165.02, 168.01, 170.01, 170.02, 244, 246, 256, 263, 317, 403, 411–413; 600/573, 576, 577

(56) References Cited

U.S. PATENT DOCUMENTS

| | | |
|---|---|---|
| 4,828,547 A | 5/1989 | Sahi et al. |
| 5,009,642 A | 4/1991 | Sahi |
| 5,120,320 A | 6/1992 | Fayngold |
| 5,192,275 A | 3/1993 | Burns |
| 5,356,392 A | 10/1994 | Firth et al. |
| 5,755,673 A | 5/1998 | Kinsey |
| 5,810,775 A | 9/1998 | Shaw |
| 5,951,520 A | 9/1999 | Burzynski et al. |
| 6,146,337 A | * 11/2000 | Polidoro et al. ............ 600/576 |

FOREIGN PATENT DOCUMENTS

| | | |
|---|---|---|
| WO | WO 98/42393 | 10/1998 |
| WO | WO 00/23130 | 4/2000 |

* cited by examiner

Primary Examiner—Nicholas D. Lucchesi
Assistant Examiner—Jennifer J Maynard
(74) Attorney, Agent, or Firm—Webb Ziesenheim Logsdon Orkin & Hanson, P.C.

(57) ABSTRACT

A safety needle assembly which is adapted for blunting of both an intravenous puncture tip and a non-patient puncture tip is provided. The needle assembly includes a cannula having a first end with an intravenous puncture tip and a second end with a non-patient puncture tip, and a blunting member in concentric relation with the cannula which includes a first blunt end proximate the intravenous puncture tip of the cannula and a second blunt end proximate the non-patient puncture tip of the cannula. An actuator is in engagement with the blunting member and the cannula. Activation of the actuator causes blunting of the intravenous puncture tip and the non-patient puncture tip by the blunting member. The needle assembly is particularly useful in connection with a blood collection system.

30 Claims, 20 Drawing Sheets

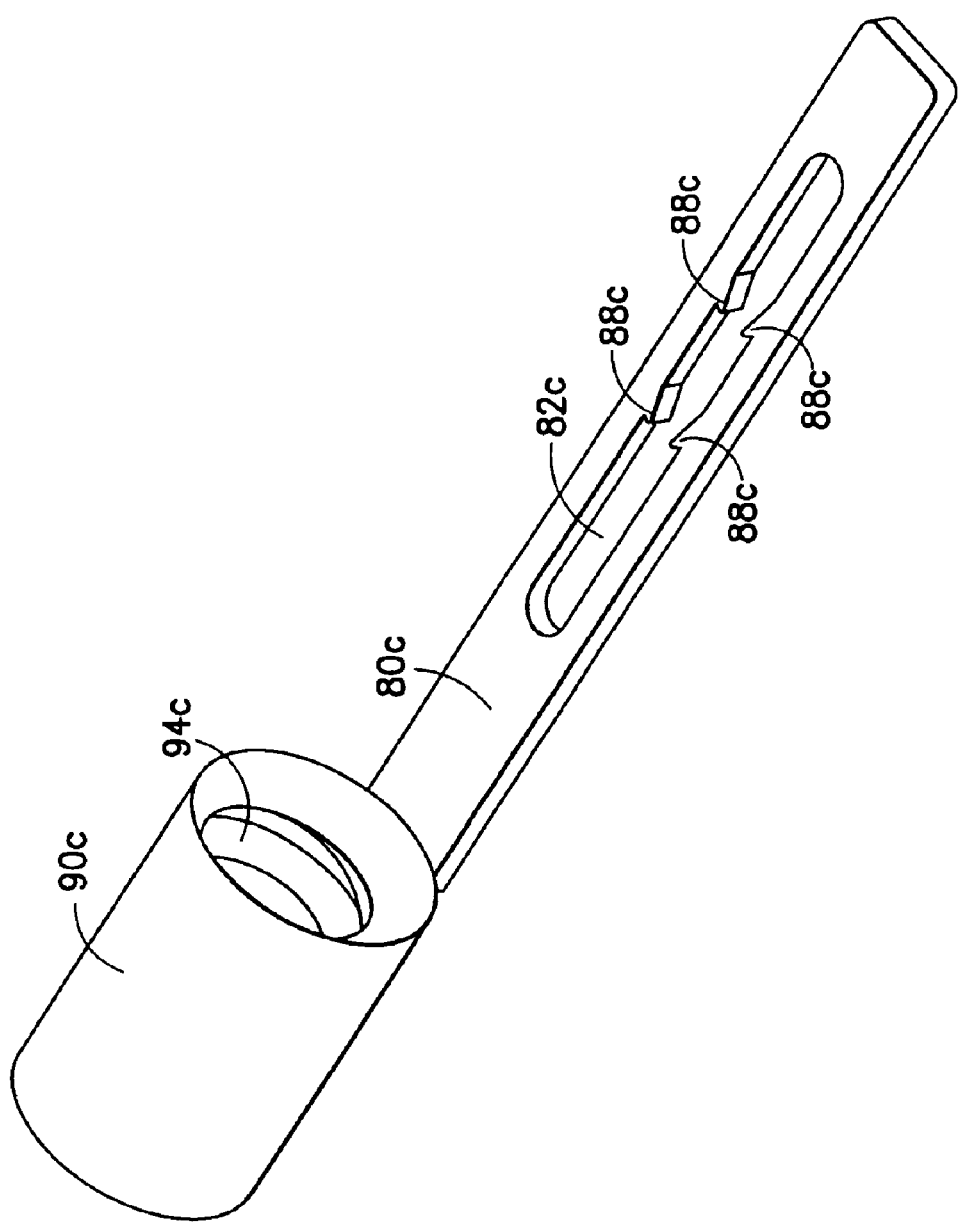

though and a hub near a central region thereof. The evacuated fluid collection tube includes a puncturable stopper at one end thereof. In this type of blood collection system, the holder typically has a housing at one end thereof for receiving the needle assembly. Likewise, the holder also has a hollow body with an opening at an opposite end thereof for receiving the collection tube. The needle assembly is rigidly received within the housing of the holder such that a first end of the needle extends forwardly of the holder for puncturing the vein of a patient. The opposite, second end of the needle extends into the hollow body of the holder. Upon assembly of the blood collection system, the needle assembly is inserted into the housing and the collection tube is inserted through the open end of the hollow body until the second end of the needle pierces the puncturable stopper of the collection tube, thereby allowing fluid communication between the interior of the collection tube and the bore which extends through the needle assembly. To draw a blood specimen from a patient using one of these blood collection systems, the evacuated collection tube is partially inserted into one end of the holder, the first end of the needle is inserted into a patient's vein and the collection tube is fully inserted into the holder such that blood will be drawn through the bore of the needle assembly and into the fluid collection tube. After drawing the specimen, the collection tube is removed so that the blood contained therein can be analyzed and the needle assembly is detached for disposal.

DUAL BLUNTING NEEDLE ASSEMBLY

The present application claims priority to U.S. Provisional Application Ser. No. 60/324,814, filed Sep. 25, 2001, entitled "Simultaneous Dual Blunting Needle Assembly".

BACKGROUND OF THE INVENTION

1. Field of the Invention

The present invention relates to needle assemblies having blunting elements for safe and convenient handling. More particularly, the present invention relates to a needle assembly having a double-ended needle for collecting or delivering fluid samples from or into a patient and which includes blunting elements for the double-ended needle.

2. Description of Related Art

Disposable medical devices having piercing elements are typically used for administering a medication or withdrawing a fluid, such as blood collecting needles, fluid handling needles and assemblies thereof. Current medical practice requires that the fluid containers and needle assemblies used in such systems be inexpensive and readily disposable. Consequently, existing blood collection systems, for example, typically employ some form of durable, reusable holder on which detachable and disposable needles and fluid collection tubes may be mounted. A blood collection system of this nature can be assembled prior to use and then disassembled after use. Thus, these blood collection systems allow repeated use of the relatively expensive holder by merely replacing the relatively inexpensive needle and/or fluid collection tube. In addition to reducing the cost of collecting blood specimens, these blood collection systems also help minimize the production of hazardous medical waste.

A popular design configuration of previously available blood collection systems includes a double-ended needle assembly, an evacuated collection tube, and a holder for maintaining the needle assembly and the collection tube in fixed relation. The double-ended needle assembly, which is also referred to as a cannula, has a bore extending therethrough and a hub near a central region thereof. The evacuated fluid collection tube includes a puncturable stopper at one end thereof. In this type of blood collection system, the holder typically has a housing at one end thereof for receiving the needle assembly. Likewise, the holder also has a hollow body with an opening at an opposite end thereof for receiving the collection tube. The needle assembly is rigidly received within the housing of the holder such that a first end of the needle extends forwardly of the holder for puncturing the vein of a patient. The opposite, second end of the needle extends into the hollow body of the holder. Upon assembly of the blood collection system, the needle assembly is inserted into the housing and the collection tube is inserted through the open end of the hollow body until the second end of the needle pierces the puncturable stopper of the collection tube, thereby allowing fluid communication between the interior of the collection tube and the bore which extends through the needle assembly. To draw a blood specimen from a patient using one of these blood collection systems, the evacuated collection tube is partially inserted into one end of the holder, the first end of the needle is inserted into a patient's vein and the collection tube is fully inserted into the holder such that blood will be drawn through the bore of the needle assembly and into the fluid collection tube. After drawing the specimen, the collection tube is removed so that the blood contained therein can be analyzed and the needle assembly is detached for disposal.

In addition to being capable of accommodating blood collection tubes, the holders of some fluid transfer systems are compatible with fluid containers having a fluid to be injected into a patient. Thus, such holders can be used to inject fluid into, as well as draw blood specimens from a patient.

In order to reduce the risk of incurring an accidental needle-stick wound, protection of the used needle tip becomes important. With concern about infection and transmission of diseases, methods and devices to enclose the used disposable needle have become very important and in great demand. Many arrangements have been designed for protecting used needle tips. For example, U.S. Pat. No. 5,951,520 to Burzynski et al., discloses a self-blunting needle in which a rod or probe-like blunting member is disposed within the bore of a needle cannula having a puncture tip suitable for puncturing tissue. To prevent accidental needle-stick wounds from occurring after use of the device, the blunting member, which is retracted behind the puncture tip when the needle is injected into tissue, can be extended beyond the puncture tip of the needle cannula to effectively blunt the puncture tip and eliminate or at least greatly reduce the risk of accidental needle-stick punctures. Such a device, however, does not provide protection for the second end of the needle at the non-patient end of the assembly.

U.S. Pat. No. 5,810,775 to Shaw discloses a collection assembly which provides for retraction of the intravenous needle at the patient end of the assembly, and further discloses a hinged cap at the open end of the housing of the holder. After drawing a specimen into a collection tube, the collection tube is removed, and the hinged cap is closed over the opening of the holder, thereby activating the needle retraction and blocking access to the second end of the needle at the non-patient end. Activation of the hinged cap and the retraction mechanism requires substantial manipulation by the user and cannot be conveniently accomplished with a single hand, as is ideal for typical phlebotomy practice. Furthermore, the size of the device is relatively large, and the retraction mechanism for the needle can cause splattering of blood when the tip of a used needle is accelerated during retraction, thus potentially exposing health care workers to blood-borne pathogens.

Accordingly, a need exists for a needle assembly which provides for safety blunting of the needle at both the intravenous and the non-patient needle points while minimizing aerosolization of blood particulates that may carry infectious diseases, and which is simple to manufacture, easy to operate and does not occupy a significant amount of disposal space.

SUMMARY OF THE INVENTION

The present invention is directed to a dual blunting needle assembly which is adapted for blunting of both an intravenous puncture tip and a non-patient puncture tip, such as for use in connection with a blood collection system.

The needle assembly of the present invention includes a cannula having a first end with an intravenous puncture tip and a second end with a non-patient puncture tip. Desirably, the first and second ends of the cannula are separate members. The assembly further includes a blunting member in concentric relation with the cannula, which includes a first blunt end proximate the intravenous puncture tip of the cannula and a second blunt end proximate the non-patient puncture tip of the cannula. An actuator is in engagement with the blunting member and the cannula. Activation of the actuator causes blunting of both the intravenous puncture tip and the non-patient puncture tip by the blunting member. In particular, the actuator causes relative axial displacement of the cannula and the blunting member with respect to each other between a non-blunted position and a blunted position in which the intravenous tip and the non-patient tip are blunted by the blunting member, such as by axial movement of either the cannula or the blunting member. Such blunting of the intravenous tip and the non-patient tip may occur simultaneously, or may occur consecutively in succession through a single activation of the actuator.

The blunting member is preferably disposed within an internal lumen of the cannula. Alternatively, the blunting member may be disposed about the cannula. The blunting member is in fixed engagement with the actuator, and the first and second ends of the cannula are axially movable with respect to the blunting member upon actuation of the actuator.

Alternatively, the first and second ends of the blunting member may be separate members, and the cannula may be in fixed engagement with the actuator. As such, the first and second ends of the blunting member are axially movable with respect to the cannula upon actuation of the actuator.

The present invention is also directed to a safety assembly which includes a needle holder and a needle assembly in engagement with the needle holder. The needle assembly preferably includes a cannula having a first end with an intravenous puncture tip and a second end with a non-patient puncture tip; a blunting member in concentric relation with the cannula which includes a first blunt end proximate the intravenous puncture tip of the cannula and a second blunt end proximate the non-patient puncture tip of the cannula; and an actuator in engagement with the blunting member and the cannula. Activation of the actuator causes blunting of both the intravenous puncture tip and the non-patient puncture tip by the blunting member.

Desirably, the first and second ends of the cannula are separate members, with the first end representing an intravenous cannula including the intravenous puncture tip, and the second end representing a non-patient cannula including the non-patient tip.

The needle assembly may be attached to the needle holder through the actuator. The actuator may include a first displacement mechanism for displacement of the intravenous cannula and a second displacement mechanism for displacement of the non-patient cannula. The first and second displacement mechanisms are preferably leads which are threaded in opposing relation with respect to each other.

A front hub assembly may also be provided for establishing engagement between the intravenous cannula and the actuator. Such a front hub assembly may include internal threads for engagement with the threaded leads of the first displacement mechanism. Moreover, an insert may also be provided for securement of the intravenous cannula to the front hub assembly.

A rear hub assembly may also be provided for establishing engagement between the non-patient cannula and the actuator. The rear hub assembly may include internal threads for engagement with the threaded leads of the second displacement mechanism. Also, the needle assembly may be attached to the needle holder through the rear hub assembly. For example, the rear hub assembly may include external threads for cooperating engagement with internal threads on the needle holder.

The actuator is rotatable about an axis defining the safety assembly, with rotation of the actuator causing the intravenous cannula and the non-patient cannula to axially displace with respect to the blunting element. The actuator may be reversibly rotatable about an axis defining the safety assembly, or may be rotatable about an axis defining the safety assembly in a single direction, thereby causing the intravenous cannula and the non-patient cannula to axially displace relative to the blunting member from the first retracted or non-blunted position to the second extended or blunted position. Also, the actuator may include a locking mechanism for preventing axial displacement of the intravenous cannula and the non-patient cannula from the second extended position to the first retracted position.

Rotation of the actuator may also cause the intravenous cannula to axially displace relative to the blunting member at a different distance than the non-patient cannula. Initial rotation of the actuator may cause the intravenous cannula to axially displace between the first retracted or non-blunted position and the second extended or blunted position, and further rotation may cause the non-patient cannula to axially displace between the first retracted or non-blunted position, and the second extended or blunted position.

The present invention is further directed to a dual blunting safety assembly which includes a needle assembly and a needle holder attached to the needle assembly. The needle assembly includes an intravenous cannula having a puncture tip and a through-hole for fluid flow therethrough, a non-patient cannula having a puncture tip and a through-hole for fluid flow therethrough, a blunting member extending between the intravenous cannula and the non-patient cannula and concentrically disposed within the through-hole of the intravenous cannula and the through-hole of the non-patient cannula. The needle assembly also includes a first blunting end for blunting the puncture tip of the intravenous cannula, a second blunting end for blunting the puncture tip of the non-patient cannula, and an actuator in fixed engagement with the blunting member and including a displacement mechanism for axial displacement of the intravenous cannula and the non-patient cannula with respect to the blunting member. Actuation of the actuator causes the intravenous cannula and the non-patient cannula to axially displace relative to the blunting member between a first retracted or non-blunted position in which the puncture tip of the intravenous cannula extends beyond the first blunting end and the puncture tip of the non-patient cannula extends beyond the second blunting end, and a second extended or blunted position in which the first blunting end extends beyond the puncture tip of the intravenous cannula and the second blunting end extends beyond the puncture tip of the non-patient cannula, thereby blunting both the puncture tip of the intravenous cannula and the puncture tip of the non-patient cannula.

DESCRIPTION OF THE DRAWINGS

FIG. 20 is a perspective view of a rear hub assembly in accordance with the alternate embodiment depicted in FIG. 12.

DETAILED DESCRIPTION

Figure 1:
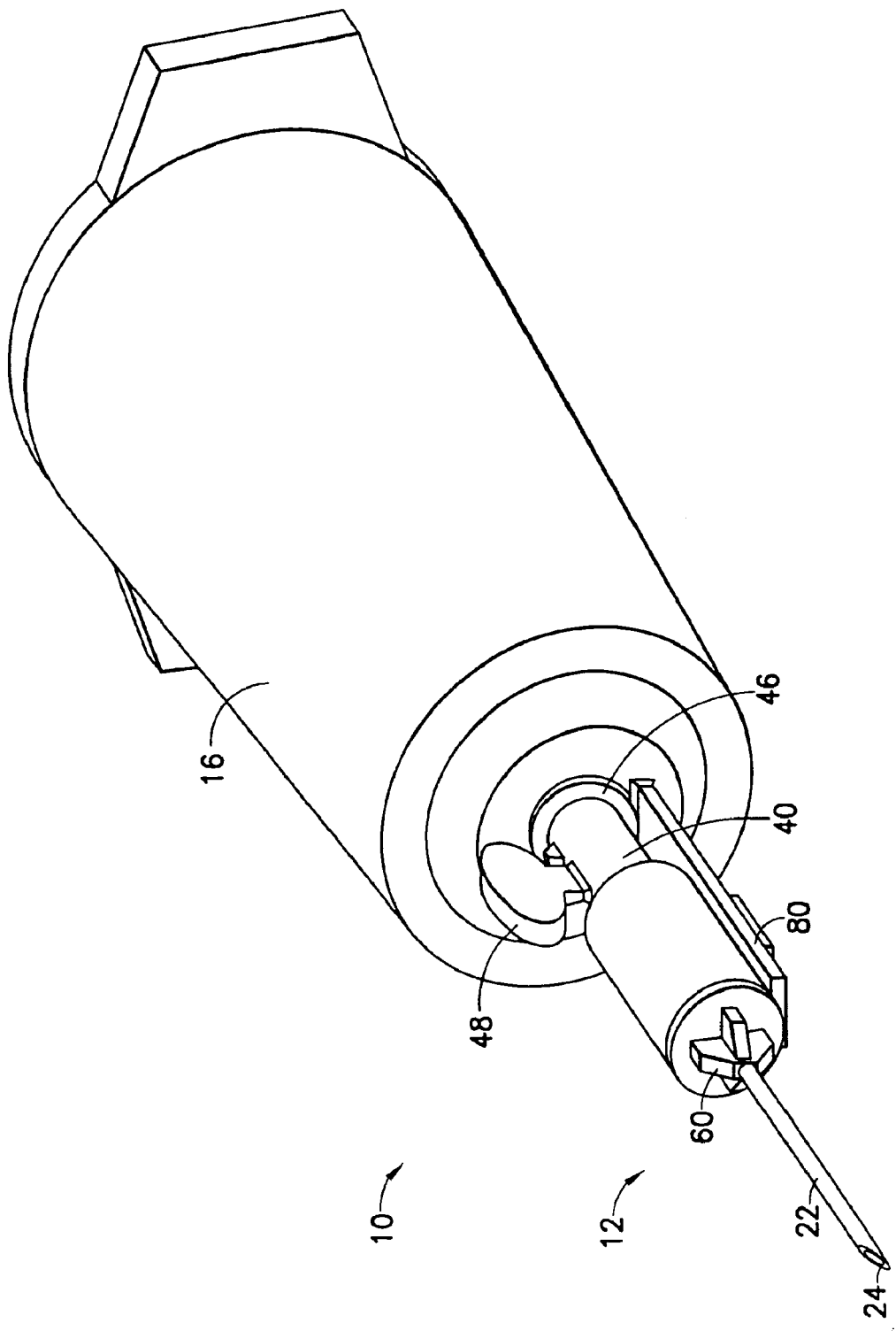
FIG. 1 is a perspective view of a safety needle assembly in accordance with the present invention shown in a non-blunted position.
Figure 2:
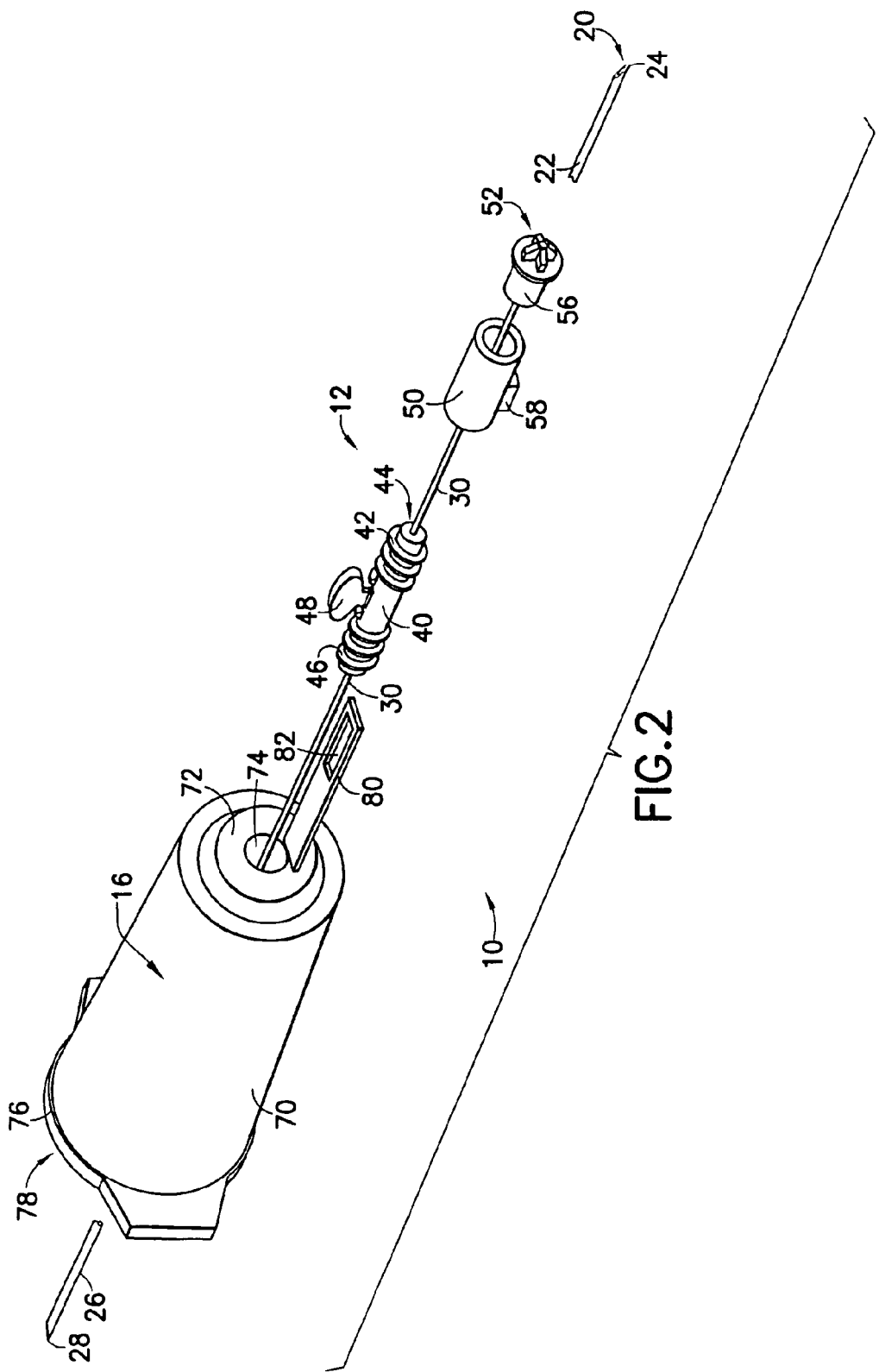
FIG. 2 is an exploded perspective view of the safety needle assembly shown in FIG. 1.
Figure 3:
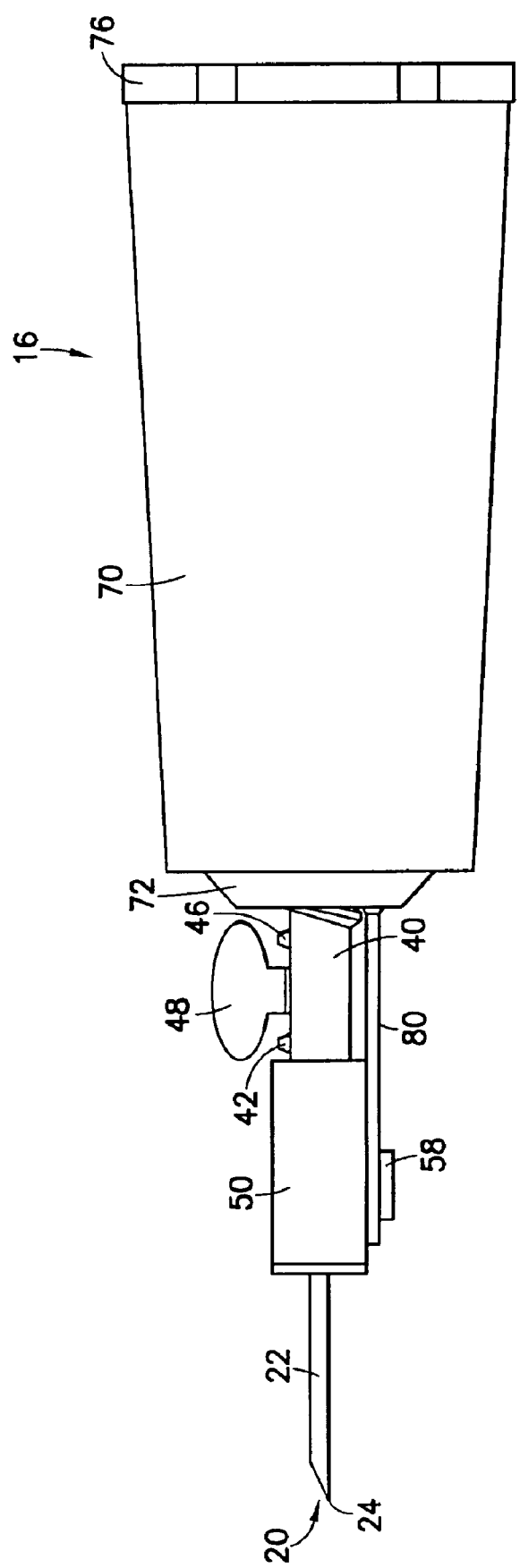
FIG. 3 is a side view of the safety needle assembly of FIG. 1.

While the present invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

Referring to the drawings in which like reference characters refer to like parts throughout the several views thereof, FIGS. 1–9 illustrate a dual blunting safety assembly in accordance with the present invention and the related features. The safety assembly includes a needle assembly in the form of a double-ended needle for use, for example, in combination with a needle holder for collecting blood samples, as is known in the art. The present invention is generally described in terms of a needle assembly, and encompasses a needle assembly as well as a safety assembly which incorporates the needle assembly and the needle holder, with the needle assembly and the needle holder including interrelating elements to provide for engagement therebetween, as will be discussed in more detail herein.

Safety assembly 10 of the present invention is shown generally at FIGS. 1–5. Safety assembly 10 includes a needle assembly 12, which is adapted for attachment to a separate needle holder 16. In this manner, needle assembly 12 can be provided as a disposable unit for use with a re-usable holder.

Needle assembly 12, generally speaking, includes a cannula having a first end with an intravenous puncture tip 24, and a second end with a non-patient puncture tip 28. A central bore or through-hole 20 extends through needle assembly 12 from intravenous puncture tip 24 to non-patient puncture tip 28, for providing the passage of fluid therethrough, and to movably accommodate blunting member 30, as will be discussed in more detail. Intravenous puncture tip 24 is provided for insertion into the vein of a patient, and non-patient puncture tip 28 is provided for puncturing of an evacuated tube, for example, during a blood collection procedure. Accordingly, intravenous puncture tip 24 is desirably shaped to provide for ease of insertion and minimal discomfort during venipuncture, such as with a tapered pointed end, as is shown in the FIGS. and is known in the art.

Desirably, the first end and second end of needle assembly 12 are provided as separate members. More particularly, needle assembly 12 is provided with a first intravenous cannula 22 having intravenous puncture tip 24, and a second non-patient cannula 26 having non-patient puncture tip 28. Second non-patient cannula 26 is further provided with an elastomeric sleeve 18 extending thereabout, and covering non-patient puncture tip 28, as is generally known in the art.

Needle assembly 12 further includes blunting member 30. Blunting member 30 includes a first blunting end 32 and a second blunting end 36 at opposing ends thereof, with a central bore or through-hole 38 extending therethrough from first blunting end 32 to second blunting end 36, for fluid flow therethrough. First blunting end 32 and second blunting end 36 are blunted such that, under ordinary hand pressure, they will not easily puncture human skin or other biological tissue.

Blunting member 30 is provided in concentric relation with the cannula of needle assembly 12. For example, blunting member 30 may extend between first intravenous cannula 22 and second non-patient cannula 26 of needle assembly 12 and be concentrically disposed within through-hole 20 of needle assembly 12, as shown generally in FIGS. 1–7. Alternatively, blunting member 30 may be provided about needle assembly 12 such that first intravenous cannula 22 and second non-patient cannula 26 of needle assembly 12 are provided within through-hole 38 of blunting member 30, as shown generally in FIGS. 10–11, and described in more detail herein.

Figure 4:
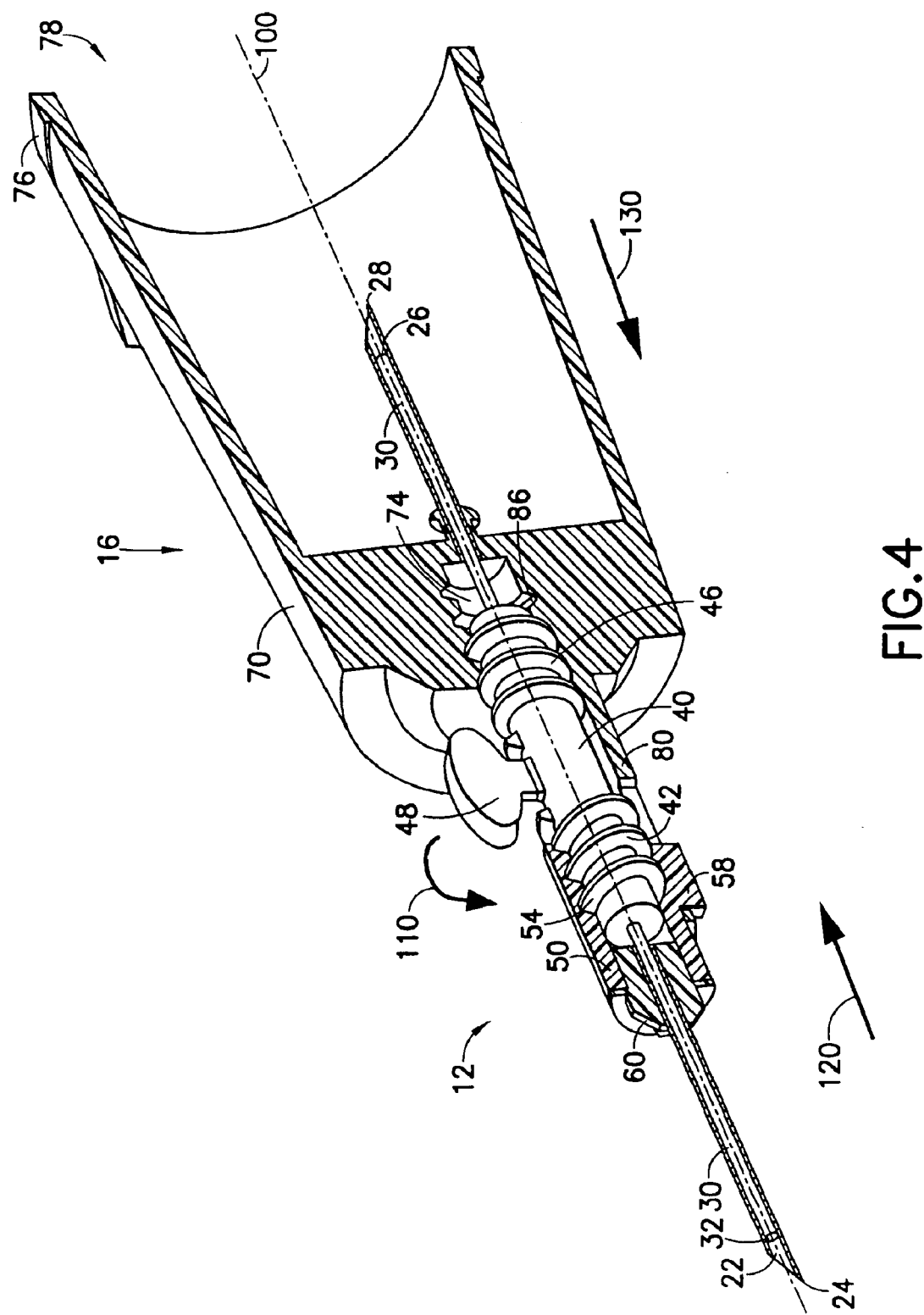
FIG. 4 is an isometric partial cross-section of the safety needle assembly of FIG. 1 in a non-blunted position.
Figure 5:
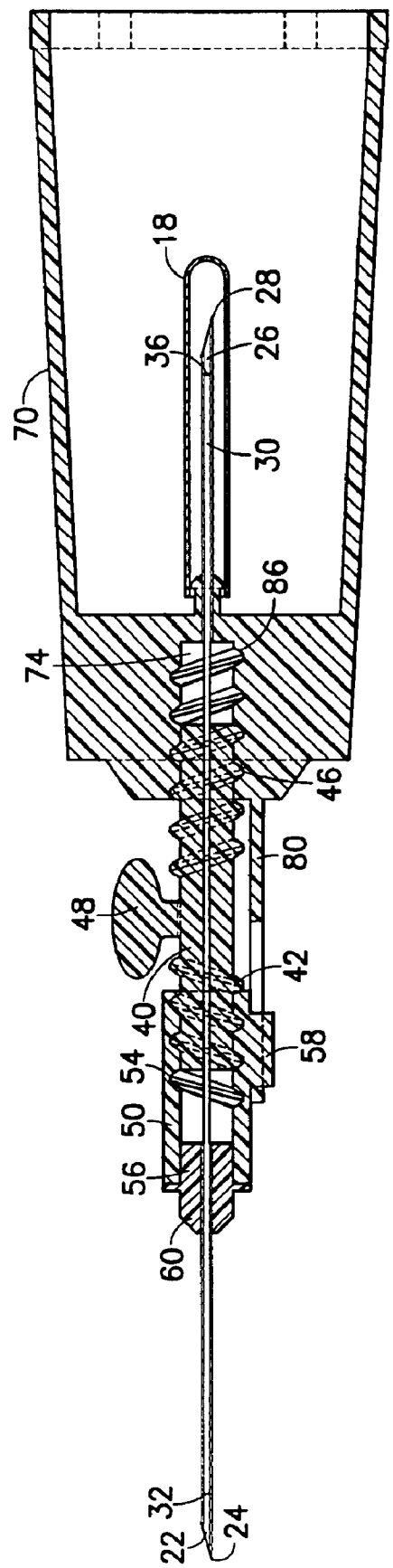
FIG. 5 is a side cross-sectional view of the safety needle assembly of FIG. 1 in a non-blunted position.
Figure 6:
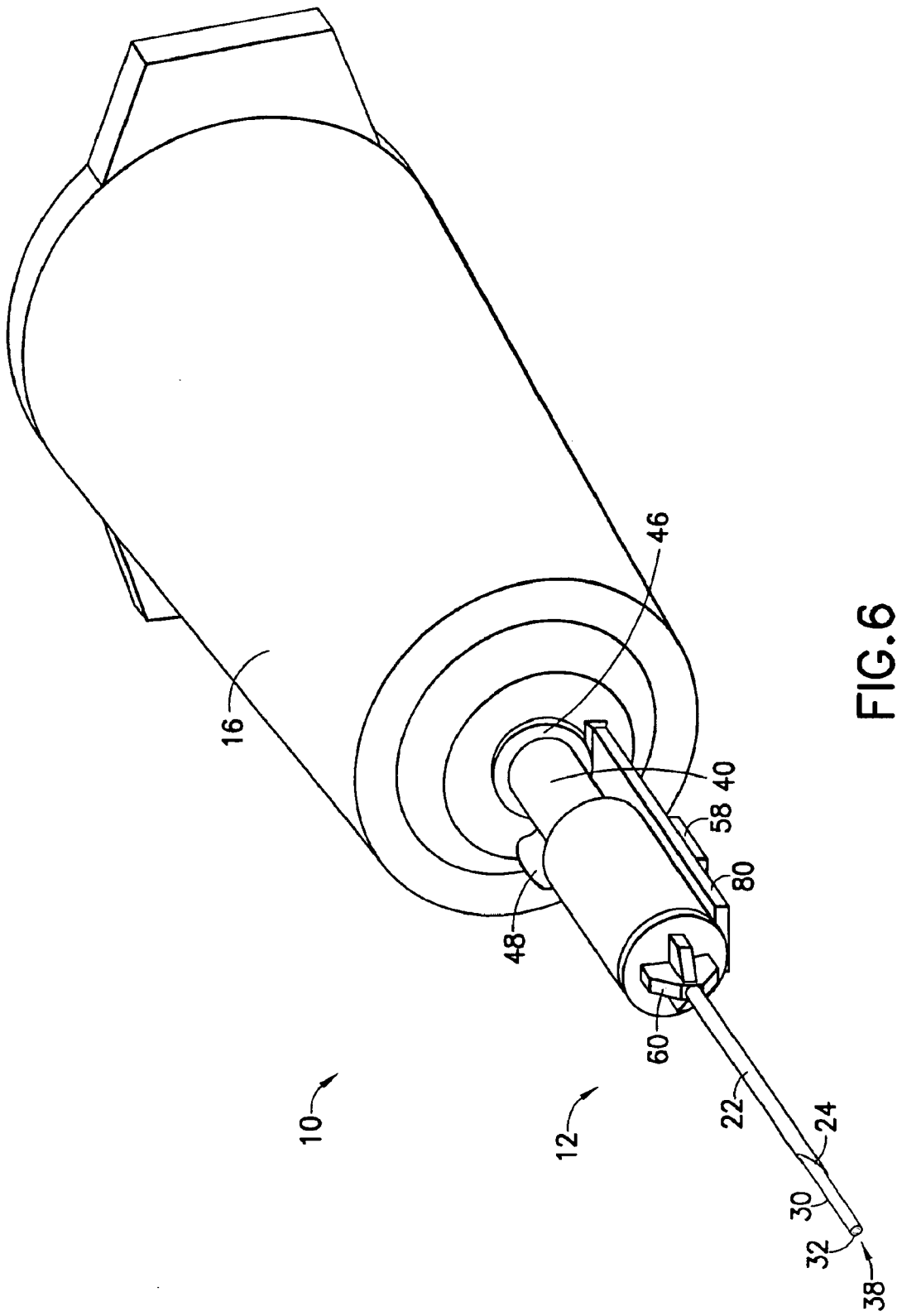
FIG. 6 is a perspective view of the safety needle assembly of FIG. 1 shown in a blunted position.
Figure 7:
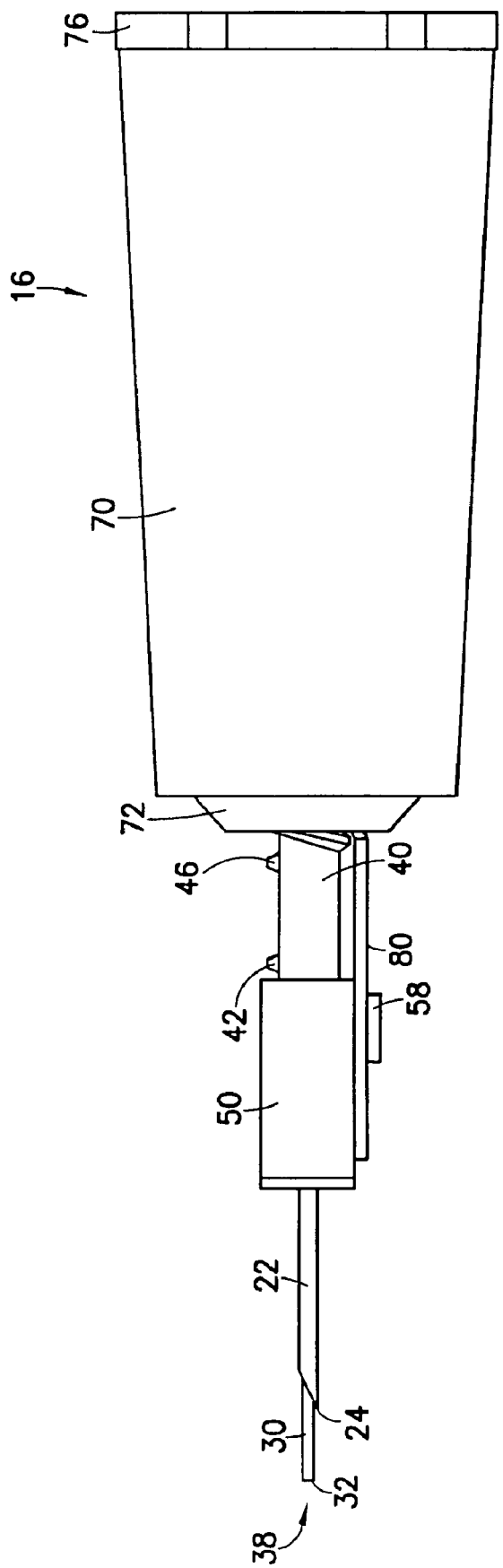
FIG. 7 is a side view of the safety needle assembly of FIG. 1 shown in a blunted position.
Figure 8:
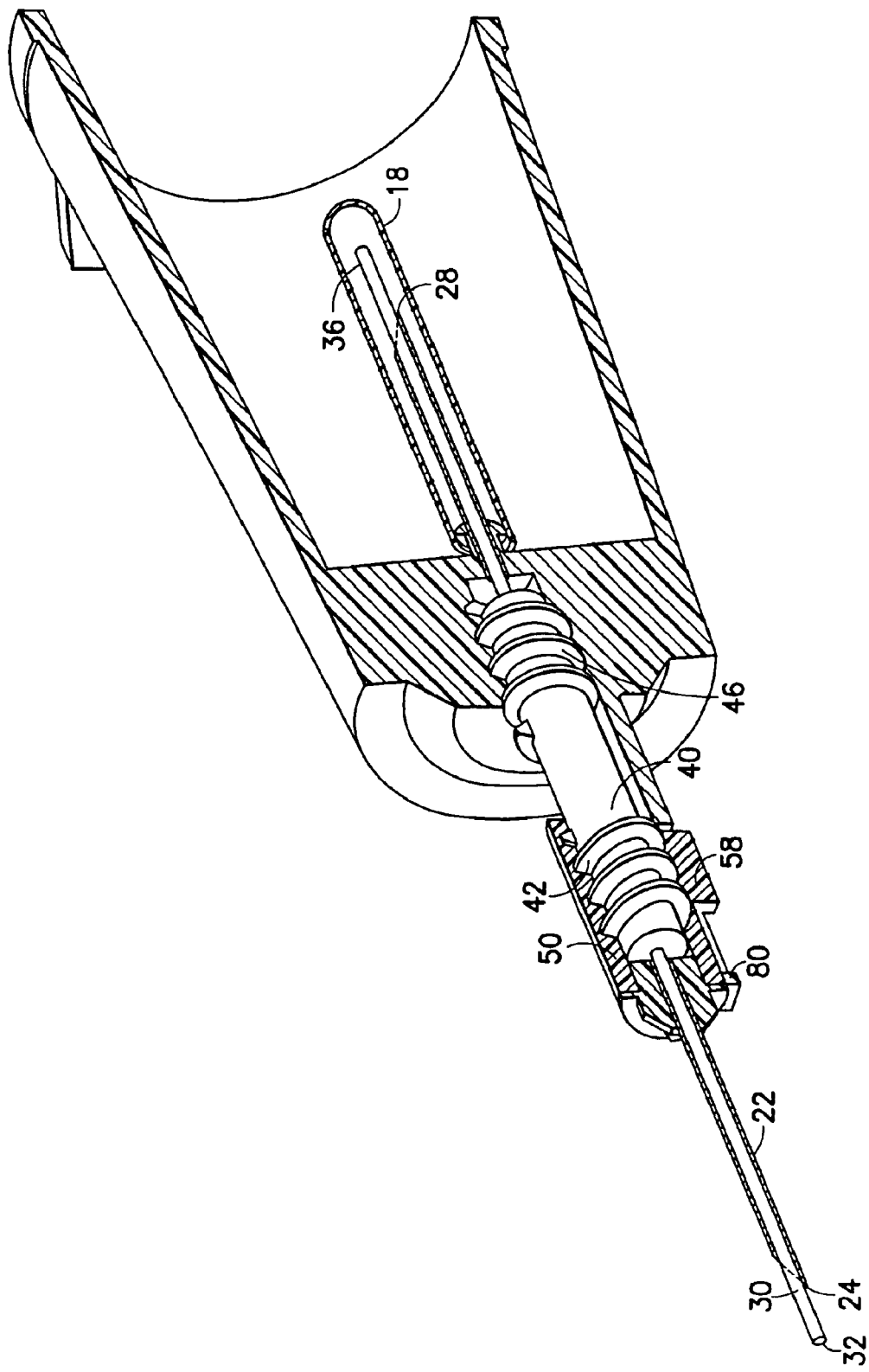
FIG. 8 is an isometric partial cross-section of the safety needle assembly of FIG. 1 in a blunted position.
Figure 9:
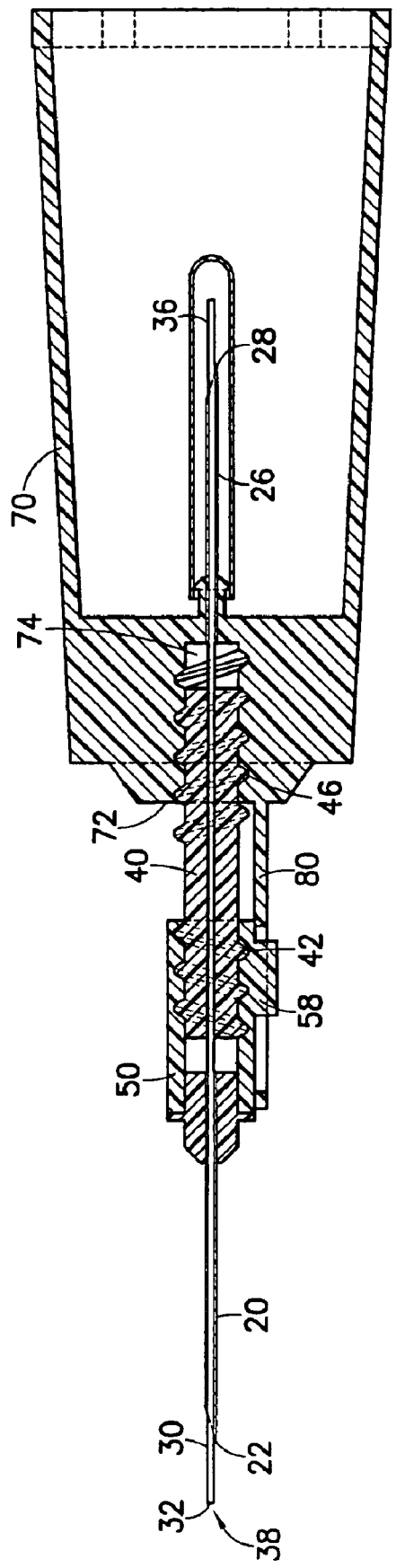
FIG. 9 is a side cross-sectional view of the safety needle assembly of FIG. 1 in a blunted position.

As best depicted in FIGS. 4–5, first blunting end 32 of blunting member 30 is adjacent or proximate first intravenous cannula 22 of needle assembly 12, and second blunting end 36 of blunting member 30 is adjacent or proximate second non-patient cannula 26 of needle assembly 12. First intravenous cannula 22 is axially slidable about first blunting end 32 of blunting member 30, and second non-patient cannula 26 is axially slidable about second blunting end 36 of blunting member 30. The inner diameter of first intravenous cannula 22 is substantially the same as the outer diameter of first blunting end 32 of blunting member 30, and the inner diameter of second non-patient cannula 26 is substantially the same as the outer diameter of second blunting end 36 of blunting member 30. As such, needle assembly 12 and blunting member 30 are dimensioned and configured for a close fit, such that the external diameter of blunting member 30 is a close fit with the internal diameter of both first intravenous cannula 22, and second non-patient cannula 26 of needle assembly 12 so that intravenous puncture tip 24 and non-patient puncture tip 28 lie flat on the surface of blunting member 30 when blunting member 30 is in an extended position, as shown in FIGS. 4–5.

Through-hole 38 of blunting member 30 allows fluid flow through needle assembly 12 during use. In alternative embodiments, however, an internal blunting member need not be hollow to accommodate fluid flow therethrough, but in such case the blunting member may have a diameter sufficiently smaller than the internal diameter of the needle cannula to allow adequate fluid flow in the annular space between them.

Further, it may be desirable to lubricate the mating surfaces of blunting member 30 and first intravenous cannula 22 and second non-patient cannula 26, as well as to provide a seal between them to prevent the unwanted flow of air bubbles. Accordingly, a drop of viscous sealant-lubricant, such as silicone oil or petroleum jelly, may be provided about the mating surfaces thereof.

Needle assembly 12 further includes an actuator 40. Actuator 40 is rotatable about an axis 100 which defines safety assembly 10. Actuator 40 includes handle 48 and an internal bore or through-hole 44 extending therethrough. Further, actuator 40 is in engagement with blunting member 30, as well as first intravenous cannula 22 and second non-patient cannula 26.

More particularly, blunting member 30 is in fixed engagement with actuator 40. For example, blunting member 30 may be integral with actuator 40, or blunting member 30 may be a separate member which is fixedly adhered to and extends within through-hole 44 of actuator 40, with first blunting end 32 and second blunting end 36 extending from opposing axial ends of actuator 40. Alternatively, blunting member 30 may be provided as two separate and discrete members, both of which are fixedly adhered to opposing axial ends of actuator 40. In such an embodiment, each of the sections of blunting member 30 has a through-hole 38, both of which are in fluid alignment with through-hole 44 of actuator 40, for providing continuous fluid communication therethrough. Blunting member 30 may be fixedly attached to actuator 40, for example, using a medical grade adhesive. Since blunting member 30 and actuator 40 are fixedly attached, rotation of actuator 40 also causes rotation of blunting member 30 within through-hole 20 of needle assembly 12.

Actuator 40 is also in engagement with needle assembly 12 through first intravenous cannula 22 and second non-patient cannula 26. In particular, actuator 40 includes structure for engagement with each of first intravenous cannula 22 and second non-patient cannula 26. Such engagement structure is adapted to provide for relative axial displacement of first intravenous cannula 22 and second non-patient cannula 26 with respect to each other, such as through a displacement mechanism. For example, actuator 40 may be provided with dual leads for displacing first intravenous cannula 22 and second non-patient cannula 26. Such dual leads are desirably provided as two sets of threads on opposing ends of actuator 40, such as first threads 42 in engagement with first intravenous cannula 22 forming a first displacement mechanism and second threads 46 in engagement with second non-patient cannula 26 forming a second displacement mechanism. While the engagement structure is discussed herein in terms of dual leads in the form of interengaging threaded surfaces, it is contemplated that such engagement structure may comprise other forms, so long as the engagement structure provides for relative axial displacement of the components as discussed. For example, it is contemplated that relative axial displacement may be achieved through any structure capable of providing actuation for relative axial displacement, such as dual camming surfaces, gears, a dual actuated piston-type structure, and the like.

First threads 42 and second threads 46 are threaded in opposing relation with respect to each other, and are desirably external threads extending about the external ends of actuator 40, respectively. As such, rotation of actuator 40 about an axis 100, such as by rotating actuator 40 in a direction of arrow 110, causes rotation of first threads 42 and second threads 46. Since first threads 42 and second threads 46 are threaded in opposing relation with respect to each other, actuation of actuator 40 about axis 100 in a direction of arrow 110 causes first threads 42 and second threads 46 to rotate in opposing threaded relation with respect to each other. Further, since first threads 42 are in engagement with first intravenous cannula 22, and second threads 46 are in engagement with second non-patient cannula 26, rotation in opposing threaded relation thereof causes displacement of first intravenous cannula 22 and second non-patient cannula 26 in opposing axial directions relative to actuator 40. Since blunting member 30 is in fixed engagement with actuator 40, such actuation of actuator 40 causes intravenous cannula 22 and non-patient cannula 26 to axially displace relative to blunting member 30 between a first retracted position in which intravenous puncture tip 24 extends beyond first blunting end 32 and non-patient puncture tip 28 extends second blunting end 36, as depicted in FIGS. 4–5, and a second extended position in which first blunting end 32 extends beyond intravenous puncture tip 24 and second blunting end 36 extends beyond non-patient puncture tip 28, as depicted in FIGS. 6–9, thereby simultaneously blunting intravenous puncture tip 24 and non-patient puncture tip 28 of needle assembly 12.

As noted, first threads 42 are in engagement with first intravenous cannula 22. Such engagement is achieved, for example, through front hub assembly 50. Front hub assembly 50 includes a central opening 52 extending therethrough. A first end of front hub assembly 50 is provided for engagement with first threads 42 of actuator 40. For example, internal threads 54 may be provided within the end of central opening 52, which internal threads 54 are capable of threaded engagement with external first threads 42 of actuator 40. A second end of front hub assembly 50 is provided for attachment to first intravenous cannula 22. Such attachment may be accomplished through hub insert 56, which attaches directly to first intravenous cannula 22 and fits within the second end of front hub assembly 50. Front hub assembly 50 is further provided with a hub arm 58, which extends from front hub assembly 50. As will be discussed in more detail, hub arm 58 provides for engagement between first intravenous cannula 22 and second non-patient cannula 26 for axial displacement therebetween.

Front hub assembly 50 may further be provided with means or structure for attachment of a needle cover (not shown), such as shoulder 60 at the second end thereof. Shoulder 60 is provided for engagement with a needle cover, which covers intravenous puncture tip 24 of first intravenous cannula 22 prior to assembling of needle assembly 12 with holder 16. Such a needle cover may be constructed of rigid polymeric material, as is known in the art. Shoulder 60 preferably includes a profile to provide for a frictional engagement with the needle cover, such that the needle cover is maintained in position about shoulder 60 in a friction fit, thereby covering and protecting first intravenous cannula 22 until assembly and use.

Second threads 46 of actuator 40 are in engagement with second non-patient cannula 26. Such engagement may be achieved, for example, directly through holder 16. For example, as depicted in FIGS. 4–9, holder 16 is defined generally by hollow body 70, which includes first end 72, and second end 76. First end 72 of holder 16 includes an opening 74 extending therethrough, while second end 76 is generally open-ended, providing holder 16 with a hollow body 70 having an internal opening 78 extending therethrough. Such internal opening 78 accommodates a blood sampling tube (not shown) during a sampling procedure, as is known in the art.

Non-patient cannula 26 is fixedly attached directly to holder 16 within internal opening 78 at first end 72 adjacent opening 74. Such attachment may be accomplished, for example, through the use of a medical grade adhesive. Actuator 40 is directly in engagement with holder 16 at opening 74. Such engagement may be provided through internal threads 86 within opening 74, which internal threads 86 are capable of threaded engagement with external second threads 46 of actuator 40. Such engagement may alternatively be provided through a snap-fit engagement or the like.

Holder 16 engages with front hub assembly 50, for establishing axial displacement between first intravenous cannula 22 and second non-patient cannula 26. For example, extension 80 may extend externally from first end 72 of body 70 in an axial direction with respect to safety assembly 10. Extension 80 may include channel 82, for slidable engagement with hub arm 58 of front hub assembly 50. During rotation of actuator 40 about axis 100, first threads 42 and second threads 46 are rotated in opposing threaded relation with respect to each other, thereby causing displacement of front hub assembly 50 and holder 16 in opposing axial directions, such as toward each other, as will be discussed in more detail herein. Thus, in such an embodiment, safety assembly 10 of the present invention encompasses a single unit, which incorporates the holder and the needle into a single assembly, with the holder and the needle including interrelating elements to provide for engagement therebetween.

Actuator 40 may be reversibly rotatable about axis 100 of safety assembly 12, thereby providing for reversibly switching between a first non-blunted position for sampling and a second blunted position for safety shielding. More desirably, actuator 40 is rotatable about axis 100 of safety assembly 10 in a single direction, such as in the direction of arrow 110. As such, intravenous cannula 22 and non-patient cannula 26 are axially displaceable relative to each other in only a single direction and, therefore, are axially displaceable relative to blunting member 30 from a first retracted or non-blunted position in which first blunting end 32 is positioned short of intravenous puncture tip 24 and second blunting end 36 is positioned short of non-patient puncture tip 28, and a second extended or blunted position in which first blunting end 32 extends beyond intravenous puncture tip 24 and second blunting end 36 extends beyond non-patient puncture tip 28.

Rotation of actuator 40 may cause simultaneous axial displacement of first intravenous cannula 22 and second non-patient cannula 26 with respect to each other, thereby causing simultaneous blunting of both first intravenous cannula 22 and second non-patient cannula 26. Alternatively, rotation of actuator 40 may cause axial displacement of first intravenous cannula 22 and second non-patient cannula 26 with respect to each other in a consecutive manner. As such, actuation of actuator 40 causes successive blunting of one of the cannulae prior to blunting of the other cannulae through a single actuation of actuator 40. For example, rotation of actuator 40 may cause axial displacement of first intravenous cannula 22 and second non-patient cannula 26 with respect to each other at a different distance with respect to blunting member 30. More particularly, it may be desirable to blunt first intravenous cannula 22 and second non-patient cannula 26 at different times, for example, by first blunting first intravenous cannula 26 after a blood sample has been collected but prior to removing first intravenous cannula 22 from the patient, and then blunting second non-patient cannula 26 after removing first intravenous cannula 22 from the patient. This may be achieved by providing blunting of first intravenous cannula 22 and second non-patient cannula 26 at different points of rotation of actuator 40. For example, during initial rotation of actuator 40 about axis 100, first intravenous cannula 22 may axially displace with respect to blunting member 30 to cause first blunting end 32 to be exposed and extend beyond intravenous puncture tip 24. Further rotation of actuator 40 about axis 100 may then cause second non-patient cannula 26 to axially displace with respect to blunting member 30 to cause blunting end 36 to be exposed and extend beyond non-patient puncture tip 28.

Such varying displacement of first intravenous cannula 22 and second non-patient cannula 26, with respect to blunting member 30, may be achieved, for example, by providing the threading of first threads 42 and second threads 46 of actuator 40 with varying pitches of threading in opposing relation. More particularly, first threads 42 may be provided at a first thread pitch and second threads 46 may be provided at a second thread pitch such that first intravenous cannula 22 axially displaces with respect to blunting member 30 in a direction toward actuator 40 and toward second non-patient cannula 26 at a faster rate than second non-patient cannula 26 axially displaces with respect to blunting member 30 in a direction toward actuator 40 and toward first intravenous cannula 22. As such, needle assembly 12 is provided in a first retracted position in which intravenous puncture tip 24 extends beyond first blunting end 32 of blunting member 30 and non-patient puncture tip 28 extends beyond second blunting end 36 of blunting member 30. Initial rotation of actuator 40 about axis 100 to an intermediate position will cause first intravenous cannula 22 to axially displace from the first retracted position to a second extended position in which first blunting end 32 of blunting member 30 extends beyond intravenous puncture tip 24. Further rotation of actuator 40 about axis 100 to a final position will cause second non-patient cannula 26 to axially displace from the first non-blunted position to a second blunted position in which second blunting end 36 of blunting member 30 extends beyond non-patient puncture tip 28. As such, both intravenous puncture tip 24 and non-patient puncture tip 28 are blunted, albeit not simultaneously, but consecutively one after the other with a single rotation of the actuator.

Such varying displacement of first intravenous cannula 22 and second non-patient cannula 26 with respect to blunting member 30 may also be achieved through other mechanisms, such as by providing first intravenous cannula 22 and second non-patient cannula 26 at different starting positions in the first non-blunted state, in addition to or instead of varying the pitch threading of first threads 42 and second threads 46. For example, blunting end 32 may be positioned closer to intravenous puncture tip 24 than blunting end 36 is positioned with respect to non-patient puncture tip 28. In this manner, rotation of actuator 40 about axis 100 will cause axial displacement of first intravenous cannula 22 and second non-patient cannula 26 in opposing directions with respect to each other and with respect to blunting member 30, which will cause first blunting end 32 of blunting member 30 to extend beyond intravenous puncture tip 24 before second blunting end 36 of blunting member 30 extends beyond non-patient puncture tip 28.

Actuator 40 may include a locking mechanism for preventing axial rotation in the reverse direction and, therefore, preventing axial displacement of intravenous cannula 22 and non-patient cannula 26 from the blunted position to the non-blunted position. For example, this may be achieved by providing first threads 42 and second threads 46 as a ratcheted threaded engagement with internal threads 54 and opening 74, respectively. Such a ratcheted threaded engagement permits threading in only one direction, thereby preventing the threads from rotating in the opposite direction.

Actuator 40 may also include a mechanism for preventing rotation of actuator 40 beyond a predetermined point. Extension 80 may work in this manner, preventing handle 48 from rotating about axis 100 of safety assembly 10 beyond a certain point. A locking mechanism for preventing axial rotation of actuator 40 in the opposite direction may be provided on extension 80, which engages handle 48 to prevent such rotation. Also, actuator 40 may be provided with means for detecting activation or rotation thereof about axis 100, such as audible, visible and/or tactile indication to identify that actuator 40 has been rotated to effect blunting of the needle assembly 12.

Operation and use of the safety assembly 10 of the present invention will now be described. In use, needle assembly 12 is provided attached to holder 16, including a needle cover (not shown) extending over intravenous cannula 22.

The needle cover extending over intravenous cannula 22 is removed. Venipuncture is then conducted in known manner, whereby intravenous puncture tip 24 is inserted into a vein of a patient, and an evacuated tube having a piercable closure is inserted into opening 78 of holder 16, such that the piercable closure of the evacuated tube contacts sleeve 18 extending about non-patient cannula 26. When pressure is exerted on the evacuated tube, the piercable closure contacting sleeve 18 causes sleeve 18 to displace, thereby causing non-patient puncture tip 28 to puncture sleeve 18 and, in turn, the piercable closure of the evacuated tube. At such time, the interior of the evacuated tube and through-hole 20 of needle assembly 12 are in fluid communication. Since the interior of the evacuated tube is at a negative pressure, blood is drawn from the vein of the patient, through through-hole 20 of needle assembly 12 and into the evacuated tube.

When all desired samples have been drawn, activation of the dual blunting needle assembly is accomplished. Activation of the dual blunting needle assembly is desirably accomplished while venipuncture is maintained, that is while intravenous cannula 22 is maintained within the vein of the patient, in order to prevent an accidental needle stick prior to blunting of the needle. Blunting of the needle assembly 12 is accomplished by rotating handle 48 of actuator 40 about the axis 100 of safety assembly 10. During rotation of actuator 40 about axis 100, first threads 42 and second threads 46 of actuator 40, which are threaded in opposing direction, are rotated in opposing threaded relation with respect to each other. With first threads 42 of actuator 40 in engagement with internal threads 54 of front hub assembly 50, and second threads 46 of actuator 40 in engagement with opening 74 of holder 16, opposing rotation of first threads 42 and second threads 46 with respect to each other causes displacement of front hub assembly 50 in a direction of arrow 120 and holder 16 in a direction of arrow 130, that is in opposing axial directions toward each other. Moreover, with extension 80 fixedly attached to holder 16, and hub arm 58 of front hub assembly 50 positioned within channel 82 of extension 80, axial rotation of front hub assembly 50 and holder 16 with respect to each other is prevented. As such, hub arm 58 can only move in slidable engagement with respect to channel 82 of extension 80 in an axial direction.

Since first intravenous cannula 22 is attached to front hub assembly 50 and since second non-patient cannula 26 is attached to holder 16, axial displacement of front hub assembly 50 and holder 16 in opposing axial directions also causes axial displacement of first intravenous cannula 22 in a direction of arrow 120 and second non-patient cannula 26 in a direction of arrow 130, that is in opposing axial directions toward each other. Moreover, since blunting member 30 is fixedly attached to actuator 40, blunting member 30 remains axially in place during rotation of actuator 40, and rotates within needle assembly 12. Since first blunting end 32 and second blunting end 36 of blunting member 30 are positioned within through-hole 20 proximate first intravenous cannula 22 and second non-patient cannula 26, respectively, movement of first intravenous cannula 22 and second non-patient cannula 26 in a direction toward each other exposes first blunting end 32 and second blunting end 36 beyond intravenous puncture tip 24 and non-patient puncture tip 28, respectively. As such, intravenous puncture tip 24 and non-patient puncture tip 28 are effectively blunted due to the blunt ends of blunting member 30 extending therebeyond. Safety assembly 10 can then be removed from the patient's vein, and appropriately discarded.

FIGS. 10–20 depict further embodiments of the present invention, and include many components which are substantially identical to the components of FIGS. 1–9. Accordingly, similar components performing similar functions will be numbered identically to those components of FIGS. 1–9, except that a suffix "a" will be used to identify those similar components in FIGS. 10–11, a suffix "b" will be used to identify those similar components in FIGS. 12–19, and a suffix "c" will be used to identify those similar components in FIG. 20.

Figure 10:
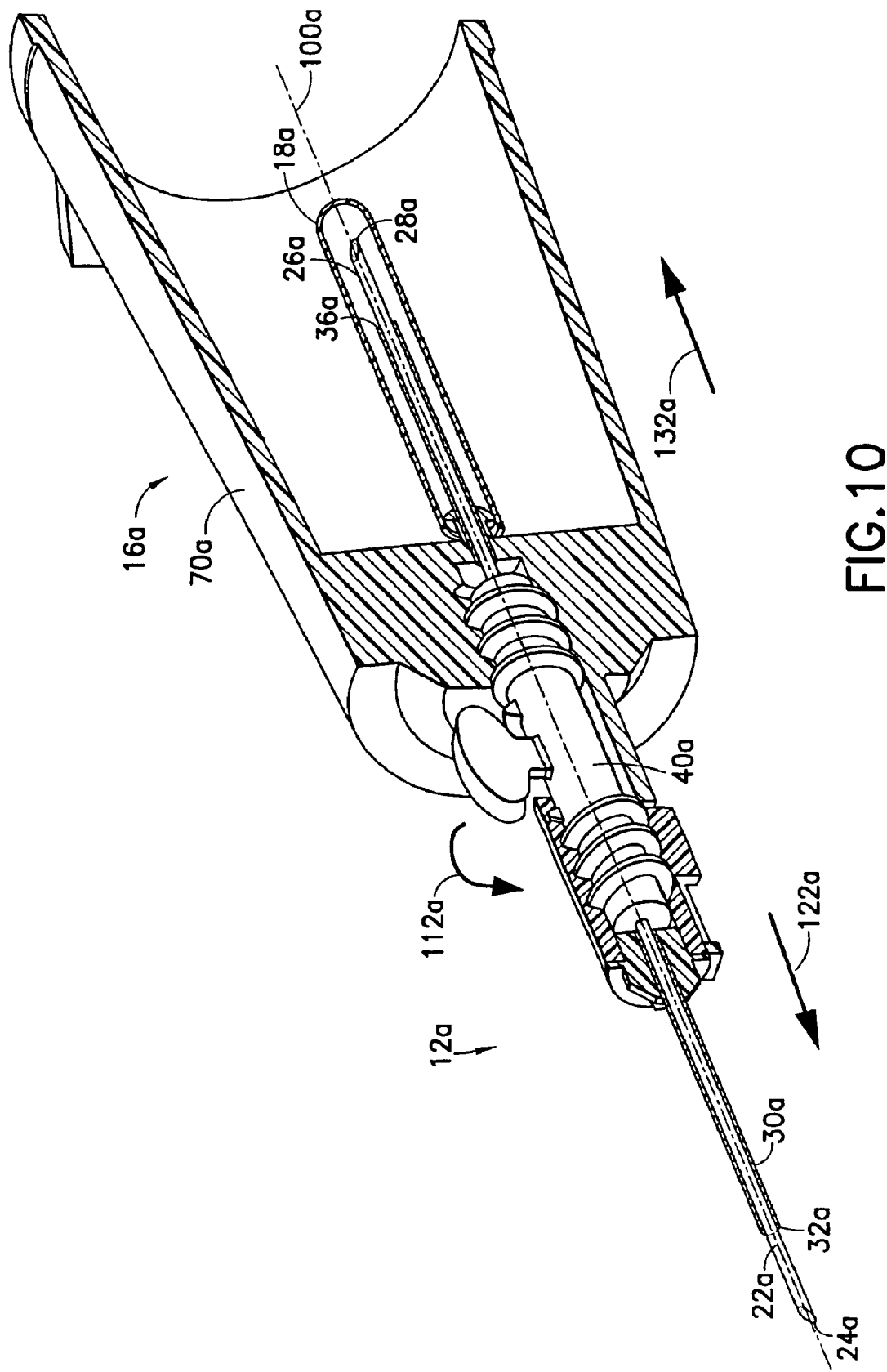
FIG. 10 is an isometric partial cross-section of a safety needle assembly in an alternate embodiment of the present invention in a non-blunted position.
Figure 11:
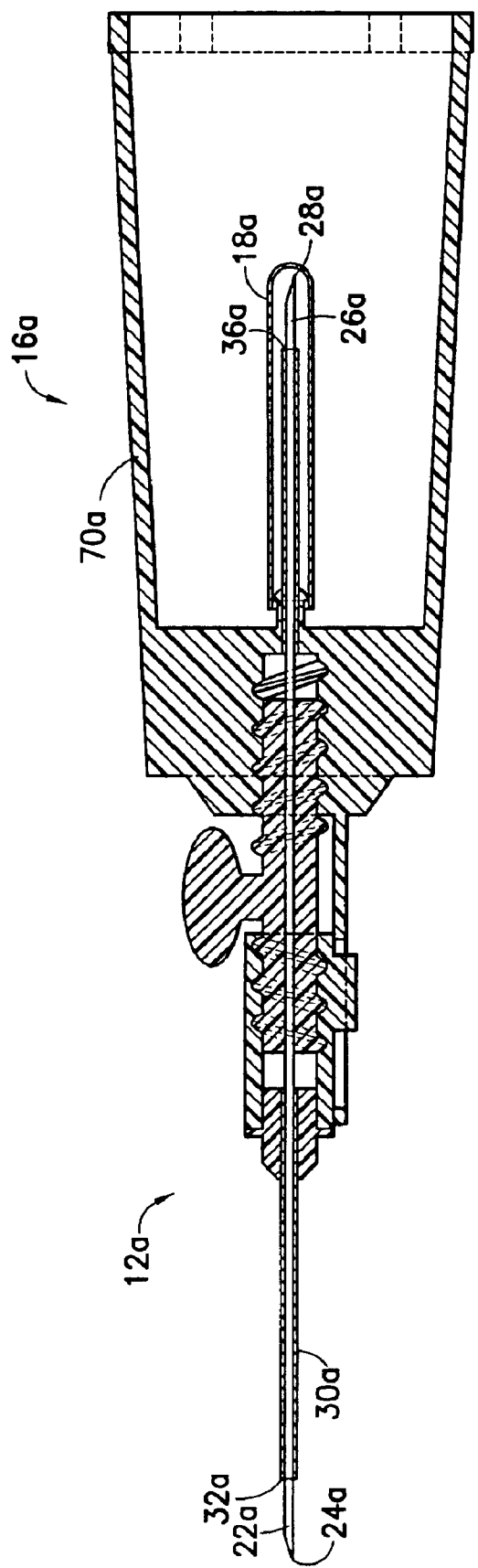
FIG. 11 is a side cross-sectional view of the needle assembly of FIG. 10 in a non-blunted position.
Figure 12:
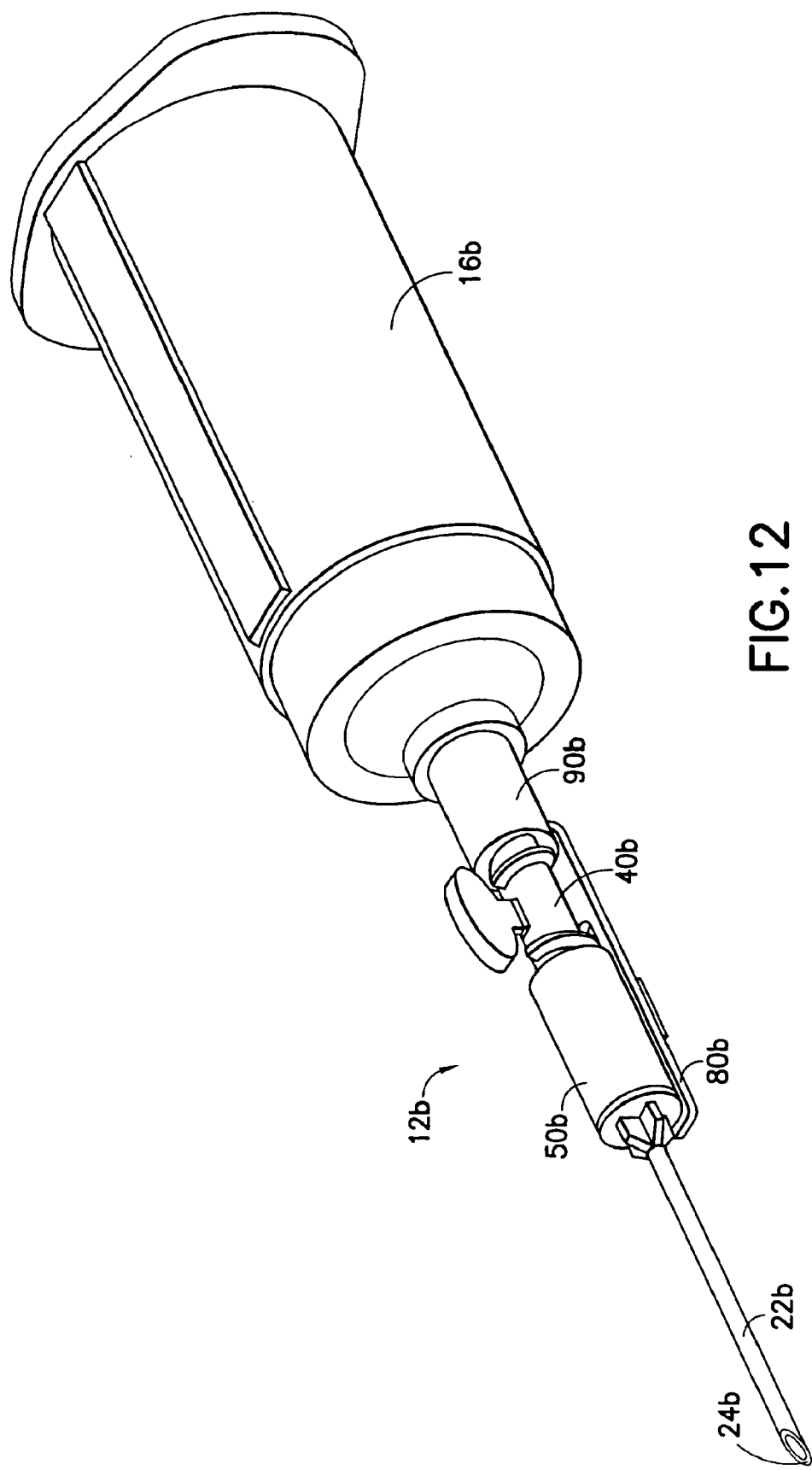
FIG. 12 is a perspective view of a safety needle assembly in accordance with an alternate embodiment of the present invention shown in a non-blunted position.
Figure 13:
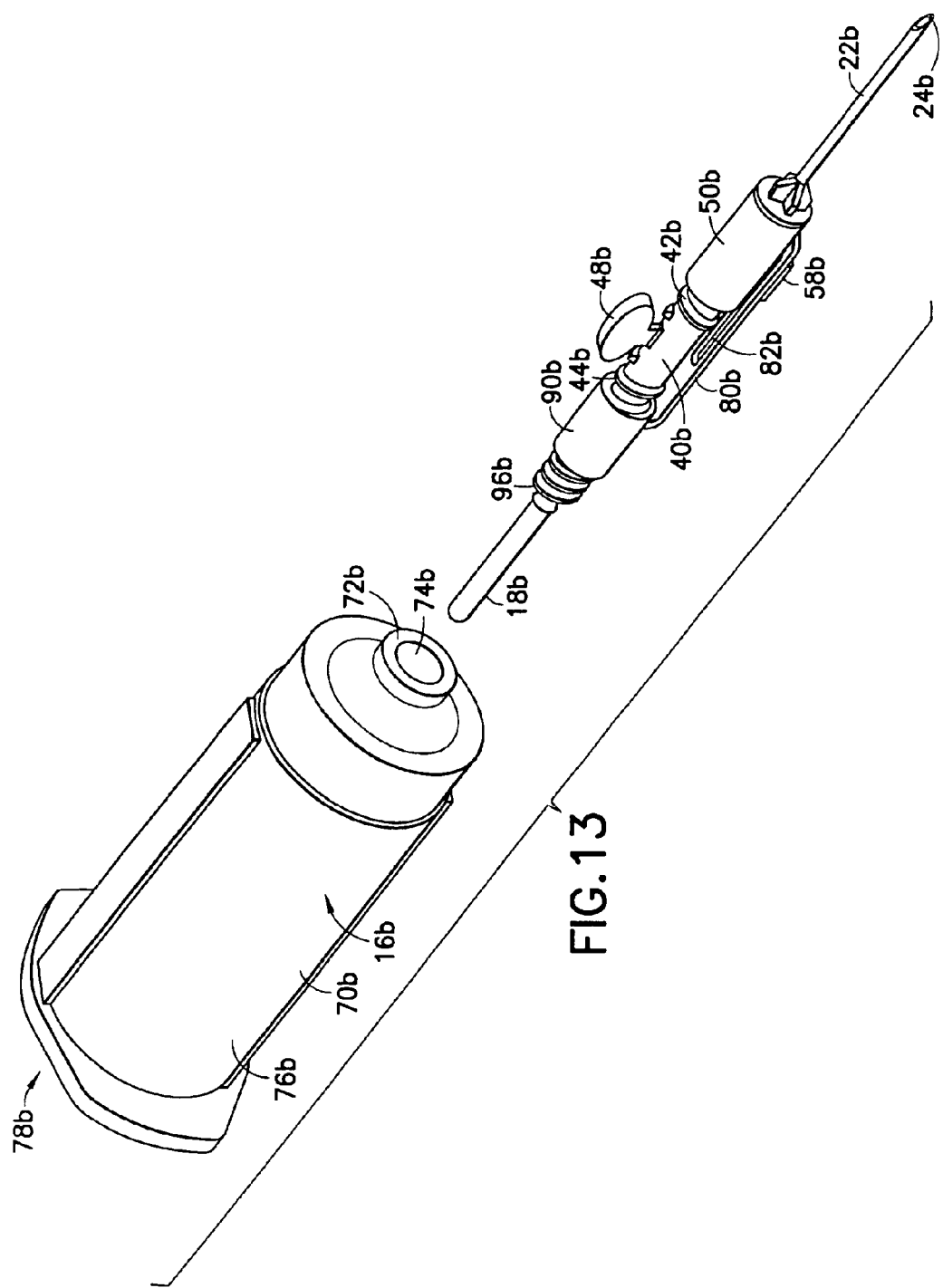
FIG. 13 is a perspective view of the safety needle assembly shown in FIG. 12 depicting the safety needle and the needle holder as separated.

As noted above, in an alternate embodiment as shown in FIGS. 10 and 11, blunting member 30a may be provided about needle assembly 12a. In such an embodiment, the cannula of needle assembly 12a is provided as a single member having a first intravenous end 22a with an intravenous puncture tip 24a, and a second non-patient end 26a with a non-patient puncture tip 28a. Further, blunting member 30a includes first blunting end 32a and second blunting end 36a as discrete and separate members. First blunting end 32a is axially slidable about the first intravenous end 22a, and second blunting end 36a is axially slidable about the second non-patient end 26a.

The cannula of needle assembly 12a is in fixed engagement with actuator 40a, while first blunting end 32a is attached to a first end of actuator 40a and second blunting end 36a is attached to a second end of actuator 40a in a similar manner as the attachment of the blunting member and the first intravenous cannula 22 and second non-patient cannula 26 discussed in the embodiment described above. For example, actuator 40a may be provided with dual leads threaded in opposing direction for displacing first blunting end 32a and second blunting end 36a with respect to each other, although such leads are desirably threaded in an opposite manner as in the embodiment described above. As such, rotation of actuator 40a about axis 100a in a direction of arrow 112a causes axial displacement of first blunting end 32a in a direction of arrow 122a and second blunting end 36a in a direction of arrow 132a, and with respect to first intravenous cannula 22a and second non-patient cannula 26a, respectively. Thus, first blunting end 32a and second blunting end 36a are axially displaced to extend beyond and encompass or surround intravenous puncture tip 24a and non-patient puncture tip 28a, respectively, thereby effectively simultaneously blunting the needle assembly.

In a further embodiment of the present invention, a standard holder for blood collection may be used with the needle assembly to provide a safety assembly. For example, as depicted in FIGS. 12–19, needle assembly 12b may be attached to a standard needle holder 16b for use in blood collection procedures. In such an embodiment, needle assembly 12b does not attach to needle holder 16b through second threads 46b as in the embodiment described above with respect to FIGS. 1–9. Instead, in the embodiment of FIGS. 12–19, needle assembly 12b is provided with rear hub assembly 90b, which provides for attaching of needle assembly 12b to a standard needle holder 16b, and which incorporates means for engagement with actuator 40b, such as internal threads 94b within rear hub assembly 90b for threaded engagement with second threads 46b of actuator 40b.

Figure 14:
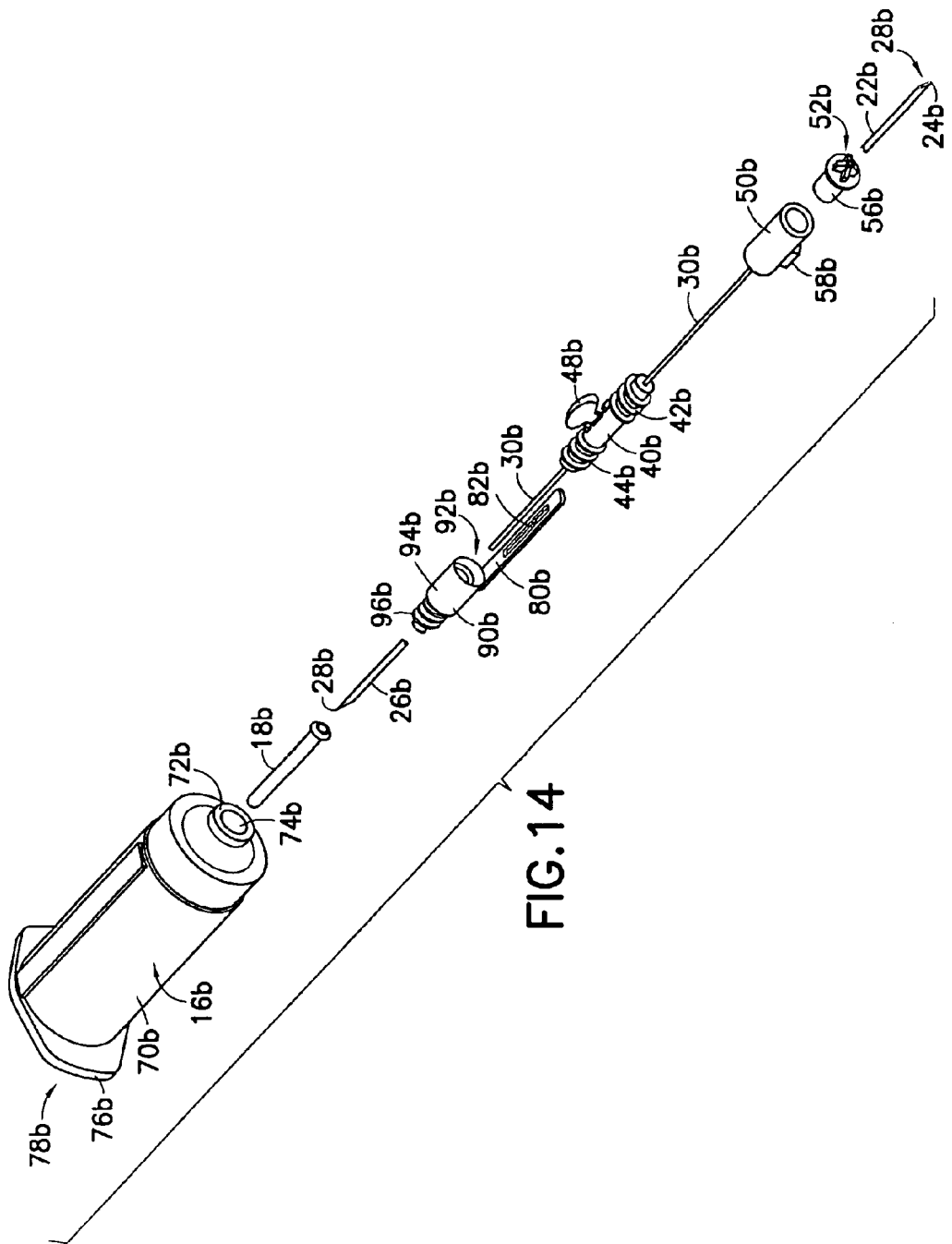
FIG. 14 is an exploded perspective view of the safety needle assembly of FIG. 12.
Figure 15:
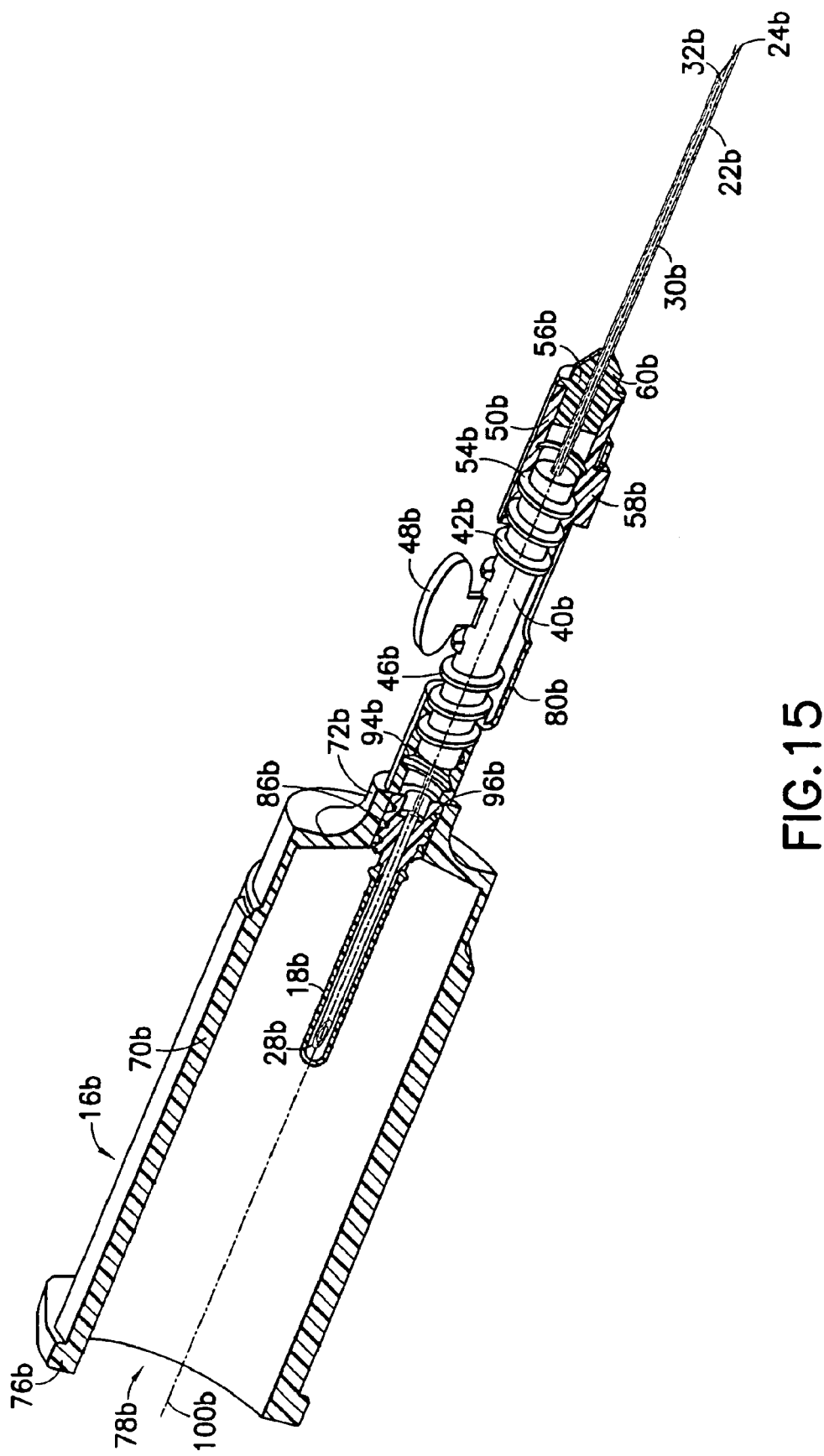
FIG. 15 is an isometric partial cross-section of the safety needle assembly of FIG. 12 in a non-blunted position.
Figure 16:
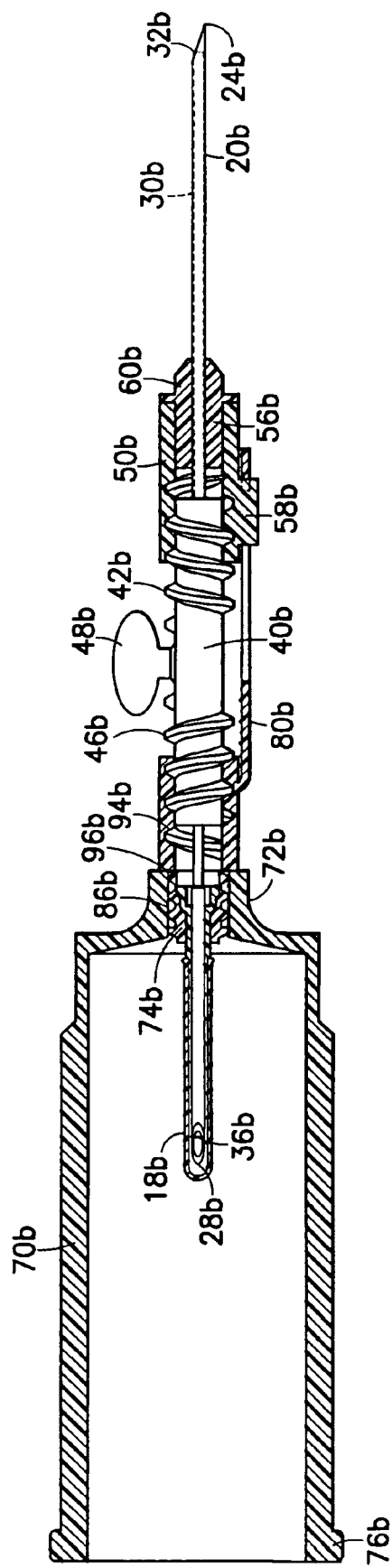
FIG. 16 is a side cross-sectional view of the safety needle assembly of FIG. 12 in a non-blunted position.
Figure 17:
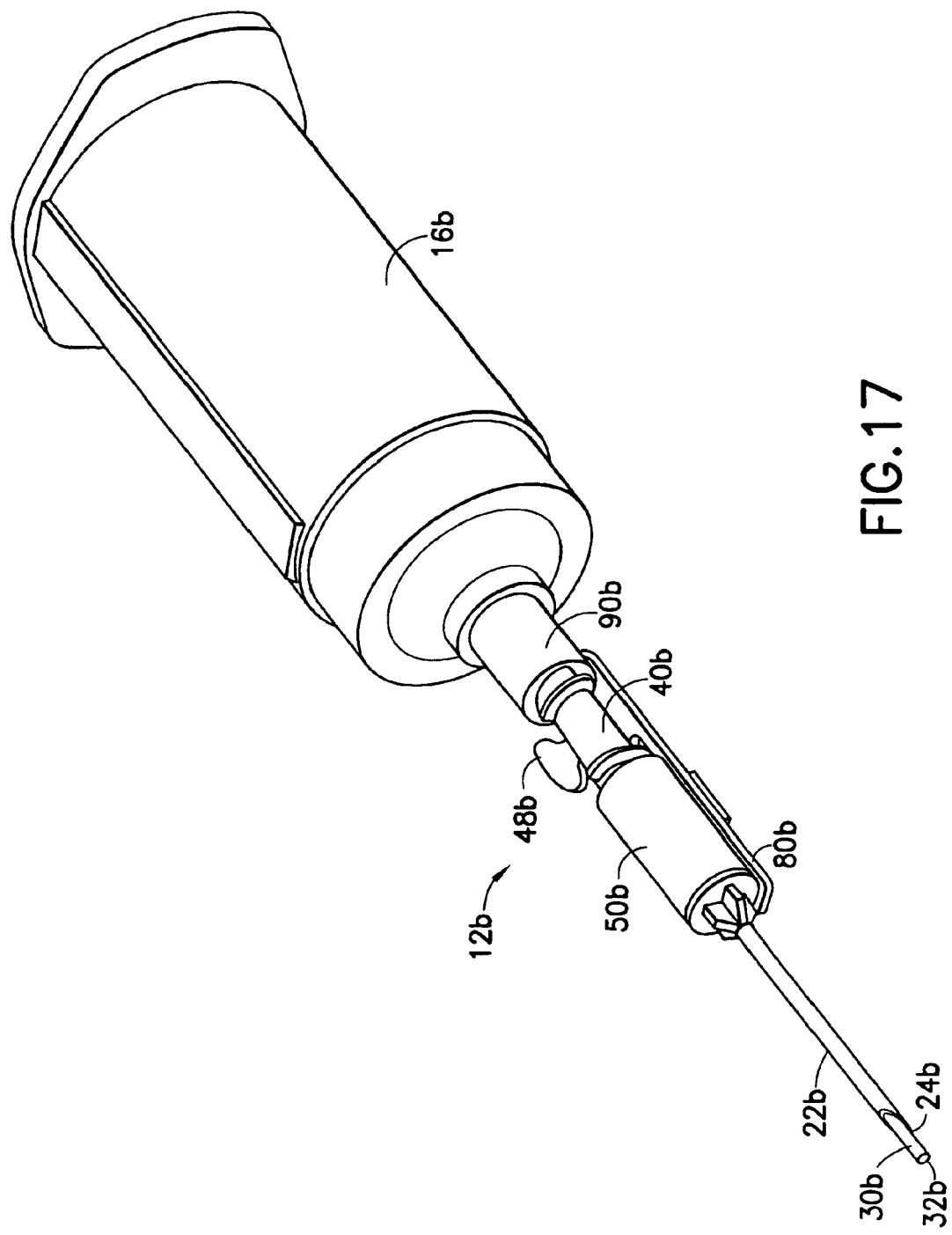
FIG. 17 is a perspective view of the safety needle assembly of FIG. 12 shown in a blunted position.
Figure 18:
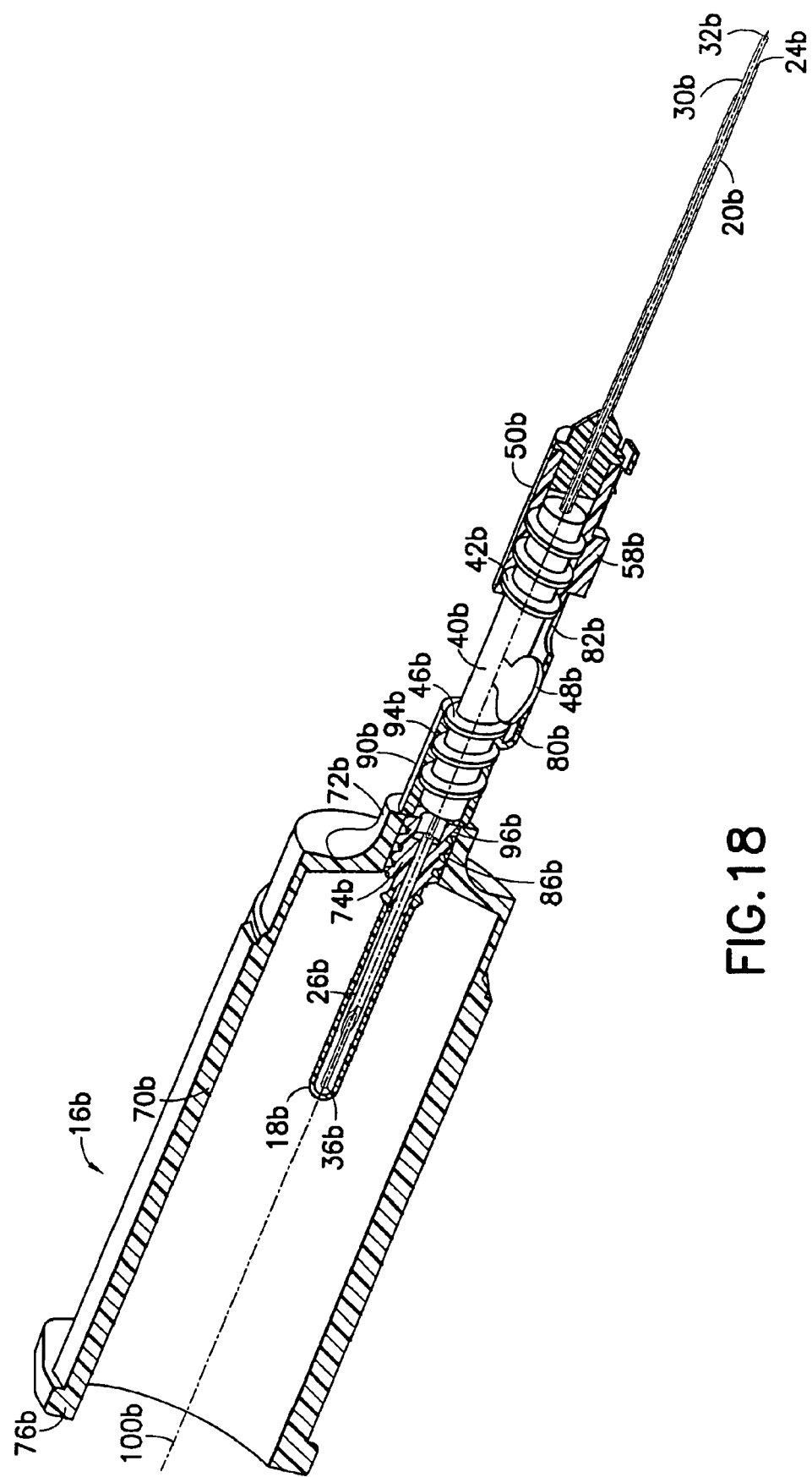
FIG. 18 is an isometric partial cross-section of the safety needle assembly of FIG. 12 in a blunted position.
Figure 19:
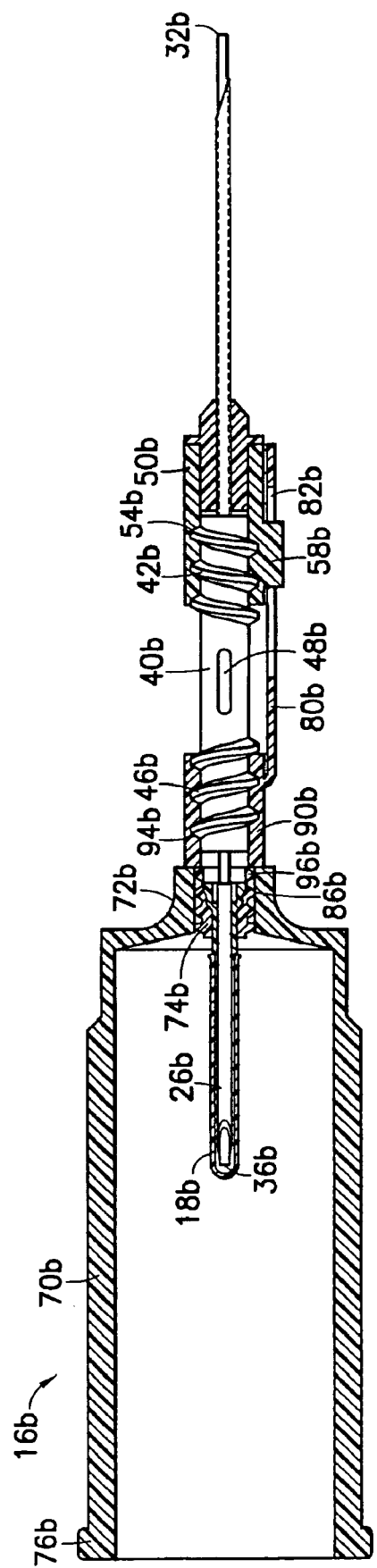
FIG. 19 is a side cross-sectional view of the safety needle assembly of FIG. 12 in a blunted position.

More particularly, as shown in the exploded view of FIG. 14, holder 16b includes a generally tubular body 70b having first end 72b and second end 76b. As with holder 16 of the embodiment described above, first end 72b includes opening 74b extending therethrough, while second end 76b is generally open ended, providing holder 16b with a hollow body 70b having internal opening 78b extending therethrough for accommodating a blood sampling tube.

In the embodiment depicted in FIGS. 1–9, second non-patient cannula 26 is fixedly attached directly to holder 16 within internal opening 78 at first end 72 adjacent opening 74, and actuator 40 is directly in engagement with holder 16 at opening 74, such as through threaded engagement between internal threads 86 and second threads 46. In the alternate embodiment of FIGS. 12–19, needle assembly 12b is provided with rear hub assembly 90b, which establishes direct engagement between second non-patient cannula 26b and actuator 40b. As such, needle assembly 12b is provided as a complete double-ended needle assembly capable of use with a standard needle holder.

As shown in detail in FIGS. 12–19, alternate needle assembly 12b includes rear hub assembly 90b. Rear hub assembly 90b includes a central opening 92b extending therethrough, and includes internal threads 94b at one end thereof and external threads 96b at the other end thereof. Internal threads 94b are provided for threaded engagement with second threads 46b of actuator 40b, while external threads 96b are provided for threaded engagement with internal threads 86b within opening 74b at first end 72b of holder 16b. Second non-patient cannula 26b is attached to rear hub assembly 90b, with sleeve 18b extending thereabout. Since second non-patient cannula 26b is directly attached to needle assembly 12b, needle assembly 12b can be provided as a separate assembly which can be attached to a standard needle holder such as holder 16b just prior to use. As such, needle assembly 12b may further be provided with a needle cover (not shown) for covering second non-patient cannula 26b during packaging and handling, which needle cover can be removed prior to assembly with holder 16b.

As noted, needle assembly 12b is attached to holder 16b through rear hub assembly 90b, particularly through external threads 96b. It is noted that such attachment may be accomplished through any attachment mechanism, such as a snap fit or interference engagement, and is desirably accomplished through a threaded engagement such as through external threads 96b in cooperating engagement with internal threads 86b.

Rear hub assembly 90b engages with front hub assembly 50b, for establishing axial displacement between first intravenous cannula 22b and second non-patient cannula 26b. For example, extension 80b may extend externally from rear hub assembly 90b in an axial direction with respect to safety assembly 10b, in a similar manner as extension 80 extends from holder 16 in the embodiment depicted in FIGS. 1–9. Extension 80b may include channel 82b, for slidable engagement with hub arm 58b of front hub assembly 50b.

As noted, internal threads 94b of rear hub assembly 90b are provided for threaded engagement with second threads 46b of actuator 40b. As such, actuation of actuator 40b by rotation about axis 100b, which causes opposing rotation of first threads 42b and second threads 46b with respect to each other as described above, also causes displacement of front hub assembly 50b and rear hub assembly 90b in opposing axial directions toward each other. Since first intravenous cannula 22b is attached to front hub assembly 50b, and since second non-patient cannula 26b is attached to rear hub assembly 90b, axial displacement of front hub assembly 50b and rear hub assembly 90b in opposing axial directions also causes axial displacement of first intravenous cannula 22b and second non-patient cannula 26b in opposing axial directions toward each other. This axial movement results in blunting of the intravenous puncture tip 24b and non-patient puncture tip 28b by the blunt ends of blunting member 30b, in a similar manner as described in connection with the embodiment of FIGS. 1–9.

It is noted that first intravenous cannula 22b and second non-patient cannula 26b may be axially displaceable with respect to each other at a different distance with respect to blunting member 30b, as discussed in the previously described embodiment. For example, this may be accomplished by providing first threads 42b and second threads 46b with different thread pitches or by positioning first intravenous cannula 22b and second non-patient cannula 26b at differing starting points, as noted above.

As discussed above, actuator 40b may include a locking mechanism for preventing axial rotation and, therefore, preventing axial displacement of intravenous cannula 22b and non-patient cannula 26b from the extended position to the retracted position, and may be provided with means for detecting activation or rotation thereof about axis 100b, such as audible, visible and/or tactile indication to identify that actuator 40b has been rotated to effect blunting of the needle assembly.

FIG. 20 depicts an exploded view of a rear hub assembly 90c in an alternate embodiment, including extension 80c and channel 82c. In order to provide such a locking mechanism and/or such audible, visible and/or tactile indication, extension 80c may be provided with fingers 88c projecting within channel 82c. In particular, as described above, rotation of actuator 40 about axis 100 causes axial displacement of first intravenous cannula 22 and second non-patient cannula 26, through axial movement of front hub assembly 50 and rear hub assembly 90 toward each other. This causes hub arm 58 to slide within channel 82. In embodiments incorporating fingers 88c within channel 82c as shown in FIG. 20, an audible and/or tactile indication is provided to the operator that the blunting mechanism has been activated when hub arm 58 slides beyond fingers 88c within channel 82c. Moreover, the shape and design of fingers 88c may prevent axial displacement of hub arm 58 within channel 82c in the opposite direction, thereby preventing reversible rotation of actuator 40, and effectively locking the needle assembly in the extended or activated blunting position.

Moreover, additional fingers may be provided within channel 82c at a further axial position therein, which are particularly useful in embodiments where first intravenous cannula 22 and second non-patient cannula 26 are axially displaceable with respect to each other at a different distance with respect to blunting member 30, as discussed above. By including such additional fingers, an indication and/or locking position may be initially provided when intravenous puncture tip 24 has been blunted by first blunting end 32, and a further indication and/or locking position may then be provided when non-patient puncture tip 28 has been blunted by second blunting end 36. It is noted that such fingers 88c may also be provided on extension 80 within channel 82 in the initial embodiment as described above with respect to FIGS. 1–9.

The safety assembly of the present invention including the needle assembly and the holder may be comprised of moldable parts which can be mass produced from a variety of materials including, for example, polyethylene, polyvinyl chloride, polystyrene or the like. Materials will be selected which will provide the proper support for the structure of the invention in its use, and which also provide a degree of resiliency for the purpose or providing the cooperative relative movement.

While the needle assembly of the present invention has been described in terms of one embodiment for use in connection with a blood collection system, it is further contemplated that the needle assembly could be used with other medical procedures, such as in conjunction with a conventional intravenous infusion set, which are well known in the art for use with conventional needle assemblies.

What is claimed:

1. A dual blunting needle assembly comprising:
   a cannula having a through-hole for fluid flow therethrough, a first end including an intravenous puncture tip and a second end including a non-patient puncture tip;
   a blunting member in concentric relation with said cannula, said blunting member having a first blunting end proximate said intravenous puncture tip and a second blunting end proximate said non-patient puncture tip; and
   an actuator in engagement with said blunting member and said cannula, wherein actuation of said actuator causes relative axial displacement of one of said cannula and said blunting member with respect to the other between a non-blunted position and a blunted position in which said intravenous puncture tip and said non-patient puncture tip are blunted by said blunting member.

2. A needle assembly as in claim 1, wherein actuation of said actuator causes said intravenous puncture tip and said non-patient puncture tip to be simultaneously blunted by said blunting member.

3. A needle assembly as in claim 1, wherein actuation of said actuator causes said intravenous puncture tip and said non-patient puncture tip to be consecutively blunted by said blunting member.

4. A needle assembly as in claim 1, wherein said blunting member is disposed about said cannula.

5. A needle assembly as in claim 1, wherein said first blunting end and said second blunting end of said blunting member comprise separate members.

6. A needle assembly as in claim 5, wherein said cannula is in fixed engagement with said actuator and said first blunting end and said second blunting end of said blunting member are axially movable with respect to said cannula upon actuation of said actuator.

7. A needle assembly as in claim 1, wherein said blunting member is disposed within said through-hole of said cannula.

8. A needle assembly as in claim 1, wherein said first end and said second end of said cannula comprise separate members.

9. A needle assembly as in claim 8, wherein said blunting member is in fixed engagement with said actuator and said first end and said second end of said cannula are axially movable with respect to said blunting member upon actuation of said actuator.

10. A needle assembly as in claim 9, wherein said actuator includes a first displacement mechanism for displacement of said first cannula member and a second displacement mechanism for displacement of said second cannula member.

11. A needle assembly as in claim 10, wherein said first and said second displacement mechanisms comprise first and second threaded leads which are threaded in opposing relation with respect to each other.

12. A needle assembly as in claim 11, further comprising a front hub assembly for establishing engagement between said first cannula member and said actuator.

13. A needle assembly as in claim 12, wherein said front hub assembly includes internal threads for engagement with said first threaded leads of said first displacement mechanism.

14. A needle assembly as in claim 12, further comprising an insert for securement of said first cannula member to said front hub assembly.

15. A needle assembly as in claim 12, wherein said front hub assembly includes structure for attachment of a needle cover.

16. A needle assembly as in claim 12, further comprising a rear hub assembly for establishing engagement between said second cannula member and said actuator.

17. A needle assembly as in claim 16, wherein said rear hub assembly includes internal threads for engagement with said second threaded leads of said second displacement mechanism.

18. A needle assembly as in claim 17, wherein said rear hub assembly includes external threads for engagement with cooperating internal threads on a separate needle holder for threaded attachment of said needle assembly to said needle holder.

19. A needle assembly as in claim 11, wherein said actuator is rotatable about an axis defining said safety assembly, and wherein rotation of said actuator causes said first cannula member and said second cannula member to axially displace with respect to said blunting member.

20. A needle assembly as in claim 19, wherein said actuator is rotatable about an axis defining said safety assembly in a single direction, thereby causing said first cannula member and said second cannula member to axially displace relative to said blunting member from a first non-blunted position in which said intravenous puncture tip extends beyond said first blunting end of said blunting member and said non-patient puncture tip extends beyond said second blunting end of said blunting member, and a second blunted position in which said first blunting end of said blunting member extends beyond said intravenous puncture tip and said second blunting end of said blunting member extends beyond said non-patient puncture tip.

21. A safety assembly as in claim 20, wherein said actuator includes a locking mechanism for preventing axial displacement of said first cannula member and said second cannula member from said second blunted position to said first non-blunted position.

22. A safety assembly as in claim 20, wherein rotation of said actuator causes said first cannula member to axially displace relative to said blunting member at a different distance than said second cannula member.

23. A safety assembly as in claim 22, wherein initial rotation of said actuator causes said first cannula member to axially displace relative to said blunting member from a first non-blunted position in which said intravenous puncture tip extends beyond said first blunting end of said blunting member to a second blunted position in which said first blunting end of said blunting member extends beyond said intravenous puncture tip, and wherein further rotation of said actuator causes said second cannula member to axially displace relative to said blunting member from a first non-blunted position in which said non-patient puncture tip extends beyond said second blunting end of said blunting member to a second non-blunted position in which said second blunting end of said blunting member extends beyond said non-patient puncture tip.

24. A needle assembly as in claim 1, further comprising structure for attaching said needle assembly to a holder capable of holding blood collection tubes.

25. A dual blunting safety assembly comprising:
   a) a needle assembly comprising:
      i) an intravenous cannula having a puncture tip and a through-hole for fluid flow therethrough,
      ii) a non-patient cannula having a puncture tip and a through-hole for fluid flow therethrough,
      iii) a blunting member extending between said intravenous cannula and said non-patient cannula and concentrically disposed within said through-hole of said intravenous cannula and said through-hole of said non-patient cannula, said blunting member including a first blunting end for blunting said puncture tip of said intravenous cannula and a second blunting end for blunting said puncture tip of said non-patient cannula, and
      iv) an actuator in fixed engagement with said blunting member and including a displacement mechanism for axial displacement of said intravenous cannula and said non-patient cannula with respect to said blunting member; and
   b) a needle holder attached to said needle assembly, wherein actuation of said actuator causes said intravenous cannula and said non-patient cannula to axially displace relative to said blunting member between a first non-blunted position in which said puncture tip of said intravenous cannula extends beyond said first blunting end and said puncture tip of said non-patient cannula extends beyond said second blunting end, and a second blunted position in which said first blunting end extends beyond said puncture tip of said intravenous cannula and said second blunting end extends beyond said puncture tip of said non-patient cannula, thereby blunting said puncture tip of said intravenous cannula and said puncture tip of said non-patient cannula.

26. A safety assembly as in claim 25, wherein said displacement mechanism comprises first and second threaded leads which are threaded in opposing relation with respect to each other.

27. A safety assembly as in claim 26, further comprising a front hub assembly including internal threads for engagement with said first threaded leads of said displacement mechanism.

28. A safety assembly as in claim 27, further comprising a rear hub assembly including internal threads for engagement with said second threaded leads of said second displacement mechanism.

29. A safety assembly as in claim 28, wherein said rear hub assembly includes external threads and said needle holder includes cooperating internal threads for threaded engagement between said needle assembly and said needle holder.

30. A safety mechanism as in claim 25, wherein said blunting member includes a through-hole.

* * * * *